United States Patent
Rohr et al.

(10) Patent No.: US 8,426,169 B2
(45) Date of Patent: Apr. 23, 2013

(54) GLYCOSYLATE DERIVATIVES OF MITHRAMYCIN, METHOD OF PREPARATION AND USES THEREOF

(75) Inventors: Jürgen Rohr, Lexington, KY (US); Irfan Baig, Lexington, KY (US); José Antonio Salas Fernández, Oviedo (ES); Alfredo Fernández Braña, Oviedo (ES); Carmen Méndez Fernández, Oviedo (ES); Mariá Pérez Solares, Oviedo (ES)

(73) Assignees: University of Kentucky Research Foundation, Lexington, KY (US); Universidad de Oviedo, Oviedo (ES)

( * ) Notice: Subject to any disclaimer, the term of this patent is extended or adjusted under 35 U.S.C. 154(b) by 678 days.

(21) Appl. No.: 12/525,695

(22) PCT Filed: Feb. 4, 2008

(86) PCT No.: PCT/ES2008/070015
§ 371 (c)(1),
(2), (4) Date: Nov. 12, 2009

(87) PCT Pub. No.: WO2008/096028
PCT Pub. Date: Aug. 14, 2008

(65) Prior Publication Data
US 2010/0086973 A1 Apr. 8, 2010

(30) Foreign Application Priority Data
Feb. 6, 2007 (ES) .................... 200700378

(51) Int. Cl.
*A61K 31/70* (2006.01)
*C07H 15/00* (2006.01)
*C12P 19/56* (2006.01)

(52) U.S. Cl.
USPC ................ 435/78; 435/886; 514/25; 536/4.1

(58) Field of Classification Search ............... 536/4.1
See application file for complete search history.

(56) References Cited

U.S. PATENT DOCUMENTS
2005/0192432 A1* 9/2005 Rohr et al. .................. 536/18.1

OTHER PUBLICATIONS

Lombo et al., The Mithracymin gene cluster of *Streptomyces argillaceus* contain a positive regulatory gene and two repeated DNA sequences that are located at both ends of the cluster, Journal of bacteriology, 1999, vol. 181, p. 642-647.*

(Continued)

*Primary Examiner* — Elli Peselev
(74) *Attorney, Agent, or Firm* — Tristan A. Fuierer; Moore & Van Allen, PLLC

(57) ABSTRACT

The present invention provides compounds characterized by the formula (I), where each of the substituent radicals is described in the specification. The invention also describes the use of said compounds in the treatment of various diseases, including: cancer or tumoral processes in general, Paget's disease, hypercalcaemia, hypercalciuria and neurological diseases (inter alia, Parkinson's, Alzheimer's, Huntington's).

(I)

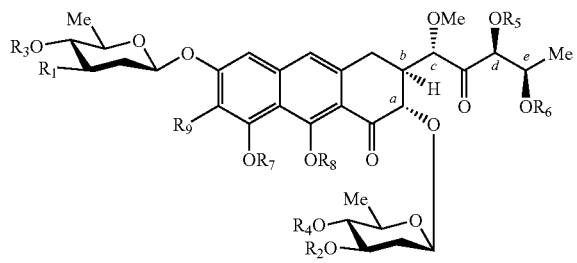

6 Claims, 4 Drawing Sheets

OTHER PUBLICATIONS

International Search Report, PCT/ES2008/070015, Apr. 25, 2008, 2 pgs.

Baig, I, et al., Mithramycin Analogues Generated by Combinatorial Biosynthesis Show Improved Bioactivity, Journal of Natural Products, 2008, pp. 199-207, vol. 71.

Fernandez Lozano, M. Jose, et al., Characterization of Two Polyketide Methyltransferases Involved in the Biosynthesis of the Antitumor Drug Mithramycin by *Streptomyces argillaceus*, The Journal of Biological Chemistry, 2000, pp. 3065-3074, vol. 275, No. 5.

Adams, V., et al., New Anti-tumor Mithramycins with Altered Saccharide Chain through Combinatorial Biosynthesis, 2005 AAPS Annual Meeting and Exposition, Nov. 2005, Abstract Only.

O'Connor, S., Aureolic Acids: Similar Antibiotics with Different Biosynthetic Gene Clusters, Chemistry & Biology, 2004, pp. 8-10, vol. 11.

Chatterjee, S., et al., Sequence-Selective DNA Binding Drugs Mithramycin A and Chromomycin A3 Are Potent Inhibitors of Neuronal Apoptosis Induced by Oxidative Stress and DNA Damage in Cortical Neurons, Annals of Neurology, Mar. 2001, pp. 345-354, vol. 49, No. 3.

Lombo, F., et al., Engineering Biosynthetic Pathways for Deoxysugars: Branched-Chain Sugar Pathways and Derivatives from the Antitumor Tetracenomycin, Chemistry & Biology, 2004, pp. 1709-1718, vol. 11.

Shashkov, A.S., et al., Structure of an antitumor antibiotic variamycin, Bioorganicheskaya Khimiya, 1991, pp. 410-416, vol. 17, No. 3, Abstract Only.

* cited by examiner (I)

(VIII) R₁ =  R₂ =  (V)

(IX) R₁ =   (VI)

(X) R₁ =   (III)

(XI) R₁ = OH  R₂ =  (VII)

(XII) R₁ = H  R₂ =  (VII)

(XIII) R₁ =  R₂ =  (IV)

(I)

| | | | |
|---|---|---|---|
| (XVII) | $R_1 = $  (II) | $R_2 = $ |  (XIV) |
| (XVIII) |  $R_1 = H$ | $R_2 = $ |  (XIV) |
| (XIX) | $R_1 = $  (II) | $R_2 = $ |  (XV) |
| (XX) |  $R_1 = H$ | $R_2 = $ |  (XV) |
| (XXI) |  $R_1 = H$ | $R_2 = $ |  (XVI) |

GLYCOSYLATE DERIVATIVES OF MITHRAMYCIN, METHOD OF PREPARATION AND USES THEREOF

CROSS-REFERENCE TO RELATED APPLICATIONS

This application is filed under the provisions of 35 U.S.C. §371 and claims the priority of International Patent Application No. PCT/ES2008/070015 filed on 4 Feb. 2008 entitled "Glycosylate Derivatives of Mithramycin, Method of Preparation and Uses Thereof" in the name of Jürgen Rohr, et al., which claims priority of Spanish Patent Application No. P200700378 filed on 6 Feb. 2007, both of which are hereby incorporated by reference herein in their entirety.

The invention belongs to the pharmaceutical field and specifically relates to compounds with application in oncology, with a chemical structure derived from mithramycin and which are obtained by microorganism fermentation.

STATE OF THE ART

Mithramycin (MTM) is an antitumor drug produced by microorganisms of the *Streptomyces* genus, including *Streptomyces argillaceus* ATCC 12956. This drug is the most important representative of the group of aureolic acid, and it is used for the treatment of testicular carcinoma, Paget's disease and hypercalcaemia caused by bone lesions associated to cancer (*Oncology* 1973, 28,147-163; *Biochem. Biophys. Res. Commun.* 1993, 195, 1245-1253; *Treat. Endocrinol.* 2002, 1, 241-257; *Treat. Endocrinol.* 2003, 2, 273-292). MTM is furthermore a neuroprotective agent which could be useful for the treatment of neurological diseases such as stroke, amyotrophic lateral sclerosis, Parkinson's disease, Huntington's disease, multiple sclerosis and viral encephalitis (*J. Neurosci.* 2004, 24, 10335-10342; *J. Biol. Chem.* 2006, 281, 16672-16680). Furthermore, MTM has antibiotic activity (*Antibiot. Chemother.* 1962, 12, 182-186).

The chemical structure of MTM is shown in FIG. 1. The group of aureolic acid compounds includes MTM, chromomycin $A_3$, olivomycin A, UCH9 and duramycin (*Appl. Microbiol. Biotechnol.* 2006, 73, 1-14). All of them contain a tricyclic core with a polyketide origin, with a highly functionalized side chain at carbon 3. The residue at carbon 7 can be a hydrogen atom or a short-chain alkyl. Likewise, these compounds have 4-6 deoxysugars linked in the form of trisaccharide or tetrasaccharide (at carbon 2) and monosaccharide or disaccharide (at carbon 6). Aureolic acid compounds differ in the nature and linking of their saccharide chains, containing different 2,6-dideoxysugars. These structural variations are responsible for the subtle differences existing among the members of the group as regards their DNA binding and their biological activity profile. It is well known that the glycosylation pattern of antitumor drugs which act by binding to DNA, as is the case of MTM, is very important in their biological activity (*Biopolymers* 2000, 54, 104-114). Therefore, obtaining novel derivatives of MTM with altered glycosidic patterns can generate drugs with improved activity.

The cluster of genes responsible for MTM biosynthesis has been widely studied (*Appl. Microbiol. Biotechnol.* 2006, 73, 1-14). MTM biosynthesis in *Streptomyces argillaceus* includes the condensation of 10 units of acyl-coenzyme A to generate a tetracyclic intermediate, called premithramycinone (FIG. 2). Then, 5 units of deoxysugars are successively added, tetracyclic intermediates with 3 sugars and with 5 sugars being generated. The glycosyltransferases MtmGIII and MtmGIV are responsible for the formation of the trisaccharide, whereas glycosyltransferases MtmGI and MtmGII catalyze the formation of the disaccharide. Finally, the cleavage of one of the rings, followed by the reduction of a keto group in the side chain, generates MTM.

There is currently a great need for novel antitumor agents, with improved activity, with fewer undesirable side effects and with higher selectivity, compared to currently used drugs. Traditionally, the pharmaceutical industry has developed novel drugs by means of two main routes: (1) search for novel natural products, and (2) chemical modification and/or synthesis of certain compounds. These methods are still useful, but usually require very important investments of resources (time, money, energy), since it is normally necessary to analyze thousands of products in order to find a novel promising compound. The development of recombinant DNA technology has opened up an interesting field of research for the generation of novel bioactive compounds by means of the manipulation of genes involved in the biosynthesis of antitumor agents, mainly of bacteria of the actinomycete group (*Trends Biotechnol.* 2001, 19, 449-456; *J. Mol. Microbiol. Biotechnol.* 2005, 9, 77-85; *Curr. Opin. Drug Discov. Devel.* 2005, 8, 748-756; *J. Ind. Microbiol. Biotechnol.* 2006, 33, 560-568; *Curr. Opin. Microbiol.* 2006, 9, 252-260). These techniques can also be used to improve the production of already known natural compounds, since natural strains usually produce low concentrations of the metabolite of interest.

DESCRIPTION OF THE INVENTION

The present invention provides novel bacterial strains derived from *Streptomyces argillaceus*. These strains are obtained by means of introducing certain additional nucleic acids in existing bacterial strains, which can be: (a) *Streptomyces argillaceus*, or (b) strains derived from *Streptomyces argillaceus*. The strains of section (b) can be obtained (among other methods) by means of the inactivation of one (or several) of the genes responsible for mithramycin biosynthesis, and are useful for obtaining derivatives of MTM (US 2005/0192432 A1; *J. Am. Chem. Soc.* 2003, 125, 5745-5753; *J. Am. Chem. Soc.* 2002, 124, 1606-1614; *Mol. Gene. Genet.* 2001, 264, 827-835; *FEMS Microbiol. Lett.* 2000, 186, 61-65; *Mol. Gene. Genet.* 2000, 262, 991-1000; *J. Biol. Chem.* 2000, 275, 3065-3074; *Mol. Gene. Genet.* 1999, 261, 216-225; *Chem. Biol.* 1999, 6, 19-30; *J. Bacteriol.* 1999, 181, 642-647; *J. Bacteriol.* 1998, 180, 4929-4937; *J. Bacteriol.* 1997, 179, 3354-3357; *Mol. Gene. Genet.* 1996, 251, 692-698; *Gene* 1996, 172, 87-91). An example of strain of section (b), which can be used in the present invention, is *Streptomyces argillaceus* M7U1, which was obtained from *Streptomyces argillaceus* by means of the inactivation of the mtmU gene (*Mol. Gene. Genet.* 2001, 264, 827-835). The mtmU gene encodes a 4-ketoreductase involved in D-oliose biosynthesis, and its inactivation results in the accumulation of premithramycinone and premithramycin A. Another example of strain of section (b) is *Streptomyces argillaceus* M7W1, which was obtained from *Streptomyces argillaceus* by means of the inactivation of the mtmW gene (US 2005/0192432 A1; *J. Am. Chem. Soc.* 2003, 125, 5745-5753). The mtmW gene encodes a ketoreductase, and its inactivation results in the accumulation of demycarosyl-MTM-SK, MTM-SA, MTM-SDK, and MTM-SK.

The introduction of nucleic acids in *Streptomyces argillaceus* (or in derivative strains) can be carried out by means of protoplast transformation, conjugation, or other known methods (such as those described in Practical *Streptomyces* genetics, The John Innes Foundation, Norwich, Great Britain, 2000), such that the nucleic acids are replicable in the organism, either in the form of an extrachromosomal element or integrated in the chromosome of the organism. Said nucleic acids encode enzymes for the biosynthesis of different sugars; said sugars are not normally produced by *Streptomyces argillaceus*. Examples of nucleic acids useful for the present invention are those contained in the following plasmids (which are mentioned by way of example): pLNBIV (*Chem. Biol.* 2002, 9, 721-729; *J. Nat. Prod.* 2002, 65, 1685-1689), pRHAM (*J. Mol. Microbiol. Biotechnol.* 2000, 2, 271-276), pLN2 (*Chem. Biol.* 2002, 9, 721-729), pLNR (*Chem. Biol.* 2002, 9, 721-729), and pFL845 (*Chem. Commun. (Camb)*. 2005 Mar. 28; (12):1604-6). The mentioned plasmids contain nucleic acids encoding enzymes for the biosynthesis of the following sugars (in the form of NDP derivatives), respectively: L-digitoxose, L-rhamnose, L-olivose, D-olivose, and D-amicetose. However, other nucleic acids which encode enzymes for the biosynthesis of other unmentioned sugars can be used in the present invention.

The bacterial strains of this invention can be cultured in any suitable medium, in conditions allowing their growth, as is described in *Gene* 1996, 172, 87-91; *J. Bacteriol.* 1998, 180, 4929-4937; *J. Am. Chem. Soc.* 2003, 125, 5745-5753. After several days of incubation, these cultures contain a high amount of cells (mycelium), together with a mixture of compounds, including derivatives of MTM. The cultures are then subjected to processes for the separation of a liquid phase (supernatant) and a solid phase (mycelium). The two phases are then subjected, separately, to several processes which can include extraction with several organic solvents, and several types of chromatography (such as HPLC, high performance liquid chromatography), for the purpose of obtaining the derivatives of MTM in the form of pure compounds. The derivatives of MTM are antitumor agents and also act as neuroprotective agents.

Likewise, the present invention provides compounds characterized by the following formula (I):

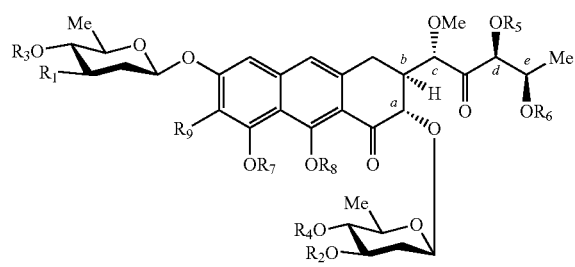

(I)

wherein $R_1$ is hydrogen, hydroxyl (OH), a hydroxyl group protected with a protecting group, a monosaccharide of formula (II)

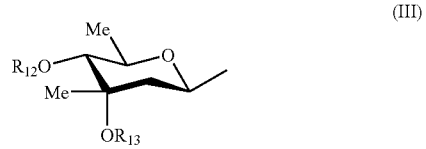

(II)

$R_2$ is hydrogen, a protecting group, a monosaccharide of formula (III),

(III)

a monosaccharide of formula (IV),

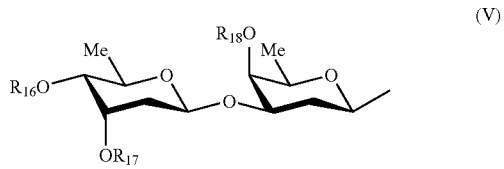

(IV)

a disaccharide of formula (V),

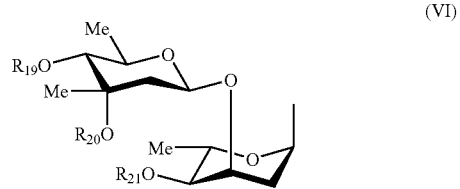

(V)

a disaccharide of formula (VI),

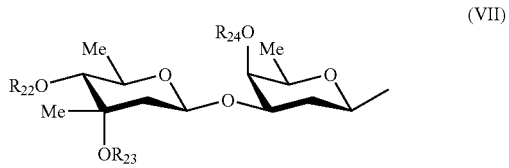

(VI)

or a disaccharide of formula (VII).

(VII)

a monosaccharide of formula (XIV), (XIV)

a disaccharide of formula (XV),

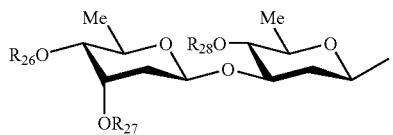
(XV)

or a disaccharide of formula (XVI)

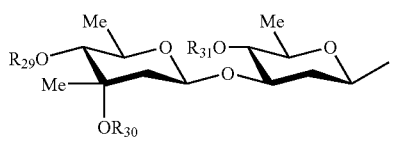
(XVI)

$R_3$, $R_4$, $R_5$, $R_6$, $R_7$ and $R_8$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$, $R_{25}$, $R_{26}$, $R_{27}$, $R_{28}$, $R_{29}$, $R_{30}$, $R_{31}$ are each and independently hydrogen or a protecting group;

$R_9$ is hydrogen, a methyl group, or an alkyl group; and
the stereochemistry of carbons a, b, c, d and e is R, S or a mixture of both.

The protecting group can consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxo group or a combination thereof.

The compounds of formula (I) include those wherein:
$R_3$, $R_4$, $R_5$ and $R_6$ are hydrogen; or
$R_3$, $R_4$, $R_5$, $R_6$, $R_7$ and $R_8$ are hydrogen; or
$R_9$ is methyl; or
the stereochemistry at carbons a, b, c and d is S, and the stereochemistry at carbon e is R; or
$R_3$, $R_4$, $R_5$, $R_6$, $R_7$, $R_8$, $R_{10}$, $R_{11}$, $R_{12}$, $R_{13}$, $R_{14}$, $R_{15}$, $R_{16}$, $R_{17}$, $R_{18}$, and $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$ are hydrogen, $R_9$ is methyl, the stereochemistry at carbons a, b, c and d is S, and the stereochemistry at carbon e is R.

In particular, the present invention provides, among others, the compounds with the following formulas (VIII, IX, X, XI, XII, XIII):

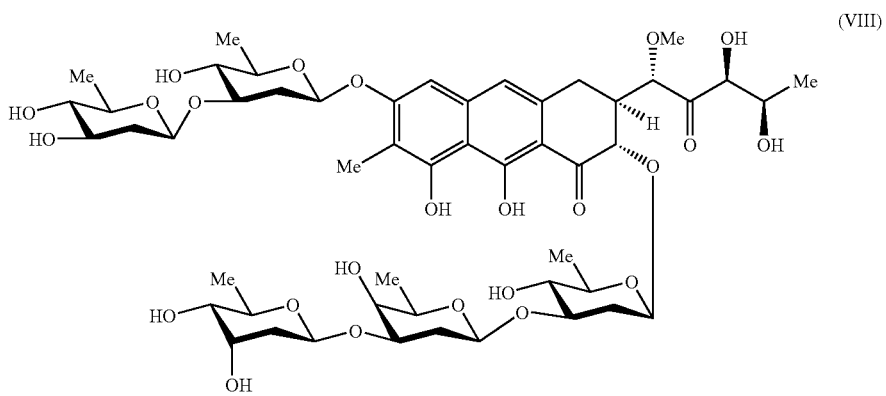
(VIII)

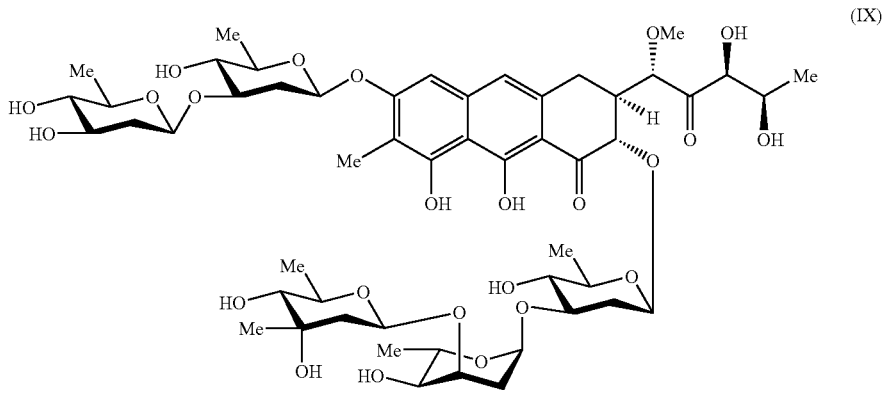
(IX)

-continued
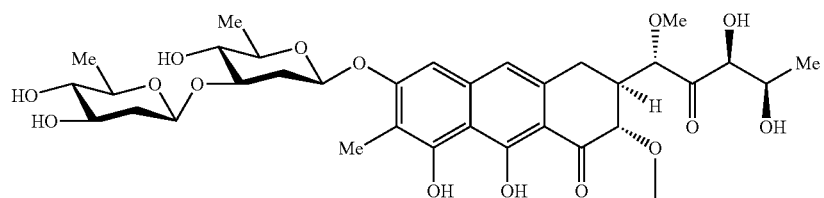
(X)
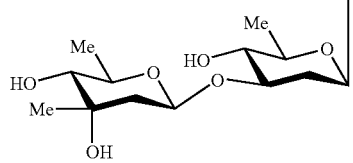
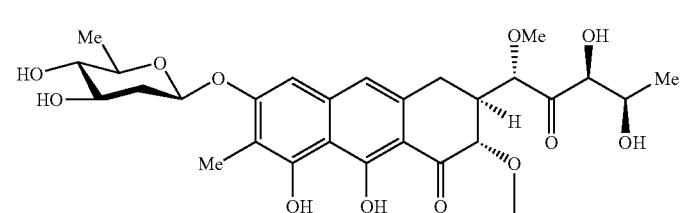
(XI)
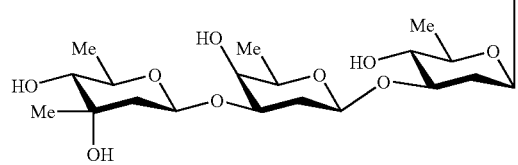
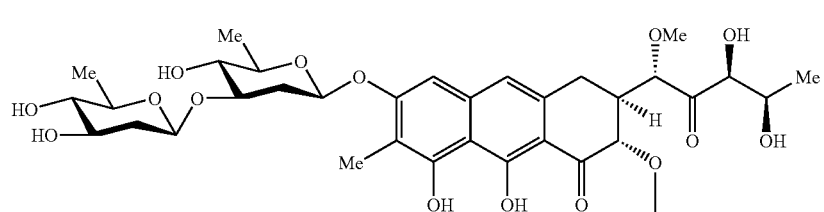
(XII)
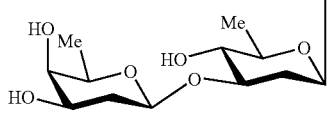
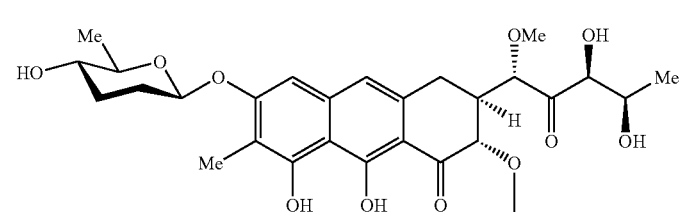
(XIII)
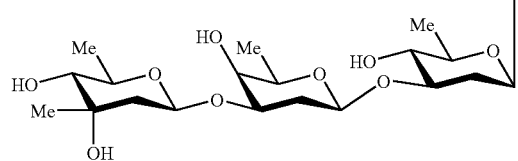

-continued
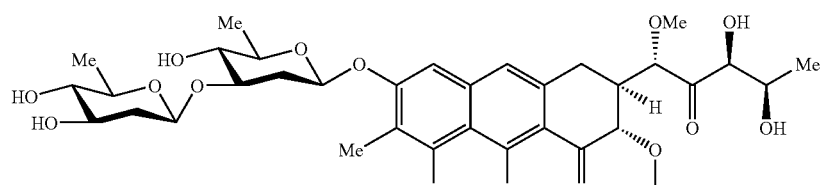
(XVII)
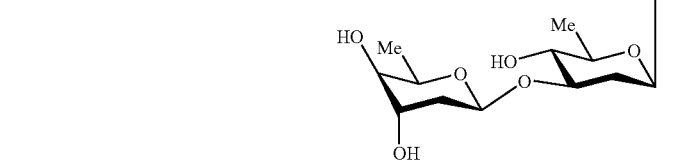
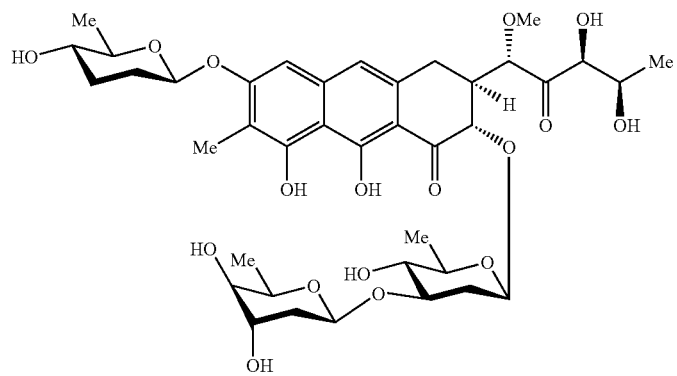
(XVIII)
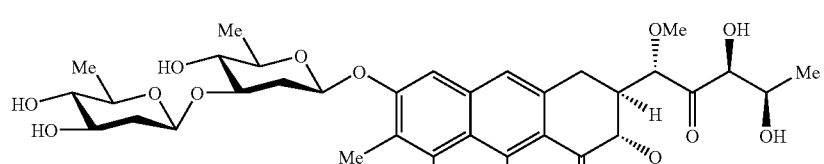
(XIX)
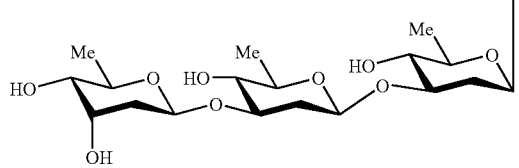
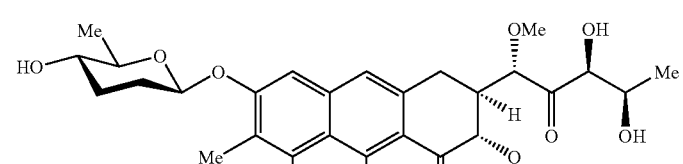
(XX)
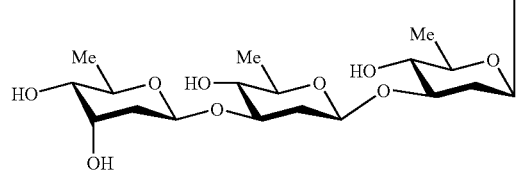

-continued

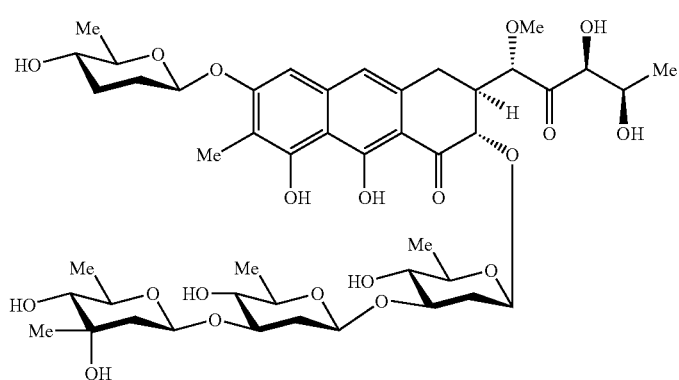

(XXI)

The compounds of the invention are tumor growth inhibitors and are therefore useful in the treatment of cancer.

Thus, the pharmaceutical compositions comprising an effective amount of a compound of formula I or a pharmaceutically acceptable salt or solvate thereof together with a pharmaceutically acceptable excipient are object of the present invention.

The use of a compound of formula I or a pharmaceutically acceptable salt or solvate thereof in the manufacture of a medicinal product is also object of the present invention.

The use of a compound of formula I or a pharmaceutically acceptable salt or solvate thereof for inhibiting the growth of a tumor is also object of the present invention.

As used herein, "inhibiting" means decreasing, slowing down or stopping. Therefore, a compound of this invention can decrease, slow down or stop the growth of a tumor cell. As used herein, "growth" means increase in size or proliferation or both. Therefore, a compound of this invention can inhibit the size increase of a tumor cell and/or can prevent the tumor cell from dividing and the number of tumor cells from increasing. A "tumor cell" is a cell forming a neoplasm (new growth), which can be cancerous (malignant) or non-cancerous (benign). A cancerous tumor cell can invade the normal tissues around it and blood/lymph vessels and form metastases in tissues far from the original tumor. In contrast, a non-cancerous tumor cell can grow and compress adjacent normal tissues but cannot invade normal tissues and blood/lymph vessels and cannot form metastases in tissues far from the original tumor.

The use of a compound of formula I or a pharmaceutically acceptable salt or solvate thereof for treating cancer is also object of the present invention.

The use of a compound of formula I or a pharmaceutically acceptable salt or solvate thereof in the manufacture of a medicinal product with antitumor activity is also object of the present invention.

The use of a compound of formula I or a pharmaceutically acceptable salt or solvate thereof in the manufacture of a medicinal product for the treatment of cancer is also object of the present invention.

A method for treating a subject, including a human being, diagnosed with cancer, consisting of treating said subject with a therapeutically effective amount of a compound of formula I or a pharmaceutically acceptable salt or solvate is also object of the present invention.

As used herein, a "subject" can include domesticated animals (for example, cats, dogs, etc.), livestock (for example, cows, horses, pigs, sheep, goats, etc.), laboratory animals (for example, mice, rabbits, guinea pigs, etc.) and birds. The subject is preferably a mammal such as a primate, and, more preferably, a human being.

In general, an "effective amount" of a compound is that amount necessary to achieve the desired result. For example, the effective amount of a compound of the present invention treats the cancer by inhibiting the growth of the cells forming the tumor, thereby preventing invasion of normal tissues and blood/lymph vessels by the tumor cells and, therefore preventing metastasis. Examples of cancers that can be treated include, but are not limited to, lung, colon, ovarian, prostate, testicular, melanoma, kidney, breast, central nervous system and leukemia. The expression "acceptable pharmaceutical composition" consists of a biologically suitable material, i.e., the material may be administered to the subject without causing substantially deleterious biological effects.

The doses or amounts of the compounds of the invention must be sufficiently large to cause the desired effect. However, the dose must not be so large that it causes adverse side effects, for example unwanted cross-reactions, anaphylactic reactions, and the like. Generally, the dose will vary with age, condition, sex and the degree of disease of the subject, and can be determined by any person skilled in the art. The dose can be adjusted by each physician, based on the clinical condition of the subject involved. The dose, dosing regimen and route of administration can be varied. The doses and the dosing regimen currently used for MTM provide a guideline for the doses and dosing regimen that can be used for the novel derivatives of MTM (see for example *Cancer Treat. Rep.* 1979, 63, 1835-1838; *Ann. Intern. Med.* 1975, 83, 659-660).

The use of a compound of formula I or a pharmaceutically acceptable salt or solvate thereof in the manufacture of a medicinal product for the treatment of Paget's disease is also object of the present invention.

A method for treating a subject, including a human being, diagnosed with Paget's disease, consisting of treating said subject with a therapeutically effective amount of a compound of formula I or a pharmaceutically acceptable salt or solvate is also object of the present invention. The subject can be a mammal, preferably a human being, and the compound can be, among other routes, parenterally administered.

The use of a compound of formula I or a pharmaceutically acceptable salt or solvate thereof in the manufacture of a medicinal product for the treatment of hypercalcaemia is also object of the present invention.

A method for treating a subject, including a human being, diagnosed with hypercalcaemia, consisting of treating said subject with a therapeutically effective amount of a compound of formula I or a pharmaceutically acceptable salt or solvate is also object of the present invention. The subject can be a mammal, preferably a human being, and the compound can be, among other routes, parenterally administered.

The use of a compound of formula I or a pharmaceutically acceptable salt or solvate thereof in the manufacture of a medicinal product for the treatment of hypercalciuria is also object of the present invention.

A method for treating a subject, including a human being, diagnosed with hypercalciuria, consisting of treating said subject with a therapeutically effective amount of a compound of formula I or a pharmaceutically acceptable salt or solvate is also object of the present invention. The subject can be a mammal, preferably a human being, and the compound can be, among other routes, parenterally administered.

The use of a compound of formula I or a pharmaceutically acceptable salt or solvate thereof in the manufacture of a medicinal product for the treatment of neurological diseases is also object of the present invention.

A method for treating a subject, including a human being, diagnosed with a neurological disease, consisting of treating said subject with a therapeutically effective amount of a compound of formula I or a pharmaceutically acceptable salt or solvate is also object of the present invention. The subject can be a mammal, preferably a human being, and the compound can be, among other routes, parenterally administered.

Examples of neurological diseases that can be treated include, but are not limited to, neurodegenerative diseases such as Parkinson's, Alzheimer's, and Huntington's diseases.

The compounds of the invention can be useful for the research in biochemistry or cell biology. For example, the compounds can be useful for blocking the expression of c-Src (and other Sp1-dependent enzymes) in osteoclasts or other cell types.

Any of the compounds of the invention can be therapeutically used forming part of an acceptable pharmaceutical composition. Any person skilled in the art can create acceptable pharmaceutical compositions, which may consist of sterile water solutions, saline solutions, or buffered solutions at physiological pH. Any of the compounds of the invention can be prepared in the form of pharmaceutical composition. The pharmaceutical compositions may include several carrier agents, thickeners, diluents, buffers, preservatives, surfactants, and others, in addition to the compound of the invention. The pharmaceutical compositions may also include active ingredients such as antimicrobial agents, anti-inflammatory agents, anesthetic agents, etc.

The compounds of the invention can be administered to the subject in several different ways depending on whether the treatment is to be local or systemic, and depending on the area to be treated. Thus, for example, a compound of the present invention can be administered in the form of ophthalmic solution, for application in the surface of the eye. Furthermore, a compound can be administered to a subject vaginally, rectally, intranasally, orally, by inhalation, or parenterally, by intradermal, subcutaneous, intramuscular, intraperitoneal, intrarectal, intra-arterial, intralymphatic, intravenous, intrathecal and intratracheal routes. Parental administration, if used, is generally carried out by means of injection. Injectables can be prepared in different forms, such as liquid solutions or suspensions, solid forms suitable for being dissolved or suspended prior to injection, or as emulsions. Other forms of parenteral administration use slow or sustained release systems, such that a constant dose is maintained (see, for example, U.S. Pat. No. 3,710,795). Preparations for parenteral administration include sterile aqueous or non-aqueous solutions, suspensions, and emulsions which may further contain buffers and diluent additives and others.

Examples of non-aqueous solvents are: propylene glycol, polyethylene glycol, vegetable oils such as olive oil, and injectable organic esters such as ethyl oleate. Examples of aqueous solvents are: water, alcoholic-aqueous solutions, emulsions or suspensions, including saline and buffered solutions. Examples of parenteral vehicles are: sodium chloride solution, Ringer's dextrose, dextrose and sodium chloride, etc. Preservatives and other additives such as, for example, antimicrobial agents, anti-oxidants, chelating agents, inert gases, etc may also be present. Formulations for topical administration may include creams, lotions, gels, drops, suppositories, sprays, liquids and powders. Certain conventional pharmaceutical carriers, aqueous, oily or powder bases, thickeners, etc. may also be necessary or desirable. Compositions for oral administration may include powders or granules, suspensions or solutions in water or non-aqueous medium, capsules or tablets. The inclusion of thickeners, flavorings, diluents, emulsifiers, dispersants, etc. may be desirable.

For the purposes of the present invention and its description, the term "derivative" of mithramycin must be interpreted as a compound covered by the general formula I. Likewise, the term "prodrug" of mithramycin must be interpreted, for the purposes of the present invention and of the description thereof, as any compound releasing mithramycin or a derivative, according to general formula I, thereof when it circulates in blood or enters the cell.

Description of a Preferred Embodiment

The following examples, described in detail, are set forth in order to better understand the present invention, which examples must be understood without a limiting character for the scope of the invention.

EXAMPLE 1

Obtaining the Bacterial Strain *Streptomyces argillaceus* (pLNBIV)

The strain *Streptomyces argillaceus* (pLNBIV) was generated by means of introducing plasmid pLNBIV in *Streptomyces argillaceus* ATCC 12956. The introduction of the plasmid was carried out by means of protoplast transformation, following standard procedures (Kieser et al., Practical *Streptomyces* genetics, The John Innes Foundation, Norwich, Great Britain, 2000). Plasmid pLNBIV has been previously described, and contains a series of genes encoding the biosynthesis of nucleosidyl diphosphate (NDP)-L-digitoxose (*Chem. Biol.* 2002, 9, 721-729; *J. Nat. Prod.* 2002, 65, 1685-1689). The strain *Streptomyces argillaceus* (pLNBIV) was deposited on 15 Nov. 2006 in the Colección Española de Cultivos Tipo (CECT) [Spanish Type Culture Collection], Universidad de Valencia, Campus de Burjassot, 46100 Burjassot (Valencia, Spain) with accession number CECT 3384.

EXAMPLE 2

Production of demycarosyl-3D-β-D-digitoxosyl-MTM (formula VIII), deoliosyl-3C-α-L-digitoxosyl-MTM (formula IX), deoliosyl-3C-β-D-mycarosyl-MTM (formula X), and 3A-deolivosyl-MTM (formula XI)

For the purification of the derivatives of MTM, the strain *S. argillaceus* (pLNBIV) was cultured in R5A medium using a two-step culture method, as has been previously described (*J. Bacteriol.* 1998, 180, 4929-4937). In the production step, eight 2 L Erlenmeyer flasks were used, each of them containing 400 ml of medium, which were incubated for 5 days. The cultures were centrifuged and filtered, and the broth was extracted in solid phase as has been described (*Chem. Biol.* 2002, 9, 519-531). The obtained fractions were analyzed by HPLC-MS using chromatographic equipment coupled to a ZQ4000 mass spectrometer (Waters—Micromass), using as solvents acetonitrile and 0.1% trifluoroacetic acid (TFA) in water, and a reversed-phase column (Symmetry C18, 2.1× 150 mm, Waters). The samples were eluted with 10% acetonitrile for the first 4 minutes, followed by a 10-88% acetonitrile linear gradient for 26 minutes, at a flow of 0.25 ml/min. Detection and spectral characterization of the peaks was carried out with a photodiode detector and Empower software (Waters). The MS analyses were carried out by means of positive-mode electrospray ionization, with a capillary voltage of 3 kV and cone voltages of 20 and 100 V. Those fractions containing derivatives of MTM (which eluted between 45 and 55 minutes) were pooled and dried under vacuum. This extract was redissolved and chromatographed in a μBondapak C18 radial compression column (PrepPak Cartridge, 25×100 mm, Waters). An isocratic elution with a mixture of acetonitrile and 0.1% TFA in water (42:58) at 10 ml/min was used. Demycarosyl-3D-β-D-digitoxosyl-MTM and 3A-deolivosyl-MTM were repurified in a semipreparative column (Symmetry C18, 7.8×300 mm, Waters) with isocratic elution with acetonitrile and 0.1% TFA in water (37:63), at 3 ml/min. Deoliosyl-3C-α-L-digitoxosyl-MTM and deoliosyl-3C-β-D-mycarosyl-MTM were also repurified using the same column and the same solvents, but changing the mixture to 45:55. In all cases, after each purification step, the collected compounds were diluted 4 times with water and desalted and concentrated by means of solid-phase extraction, in order to be finally lyophilized. Thus, 14.3 mg of demycarosyl-3D-β-D-digitoxosyl-MTM (formula VIII), 5.8 mg of deoliosyl-3C-α-L-digitoxosyl-MTM (formula IX), 3.3 mg of deoliosyl-3C-β-D-mycarosyl-MTM (formula X), and 10.9 mg of 3A-deolivosyl-MTM (formula XI) were obtained.

The products were characterized by means of NMR spectroscopy and mass spectrometry. The electrospray ionization mass spectra (ESI-MS) were acquired using a Thermo Finnigan LCQ mass spectrometer, with sample introduction by direct diffusion. The high-resolution positive-mode fast atom bombardment (FAB) mass spectrometry was acquired using a VG70SQ model mass spectrometer (with double-focusing magnetic sector). The pseudomolecular ion MS-MS spectrometry was performed in both +ve and −ve modes to study the fragmentation pattern of the molecule. The UV spectra were obtained with a Varian CARY 50 spectrometer, and the IR spectra were obtained from KBr discs in a Nicolet Magna IR-560 spectrometer. All the NMR data were obtained in pyridine d5, using a 400 MHz Varian Inova instrument, except the $^{13}$C broadband spectra, which were obtained at 50.3 and 75.4 MHz in 200 and 300 MHz Varian Inova spectrometers, respectively. The δ values were adjusted with reference to the solvent peaks (δ 8.74 ppm and δ 150.35 ppm for $^{1}$H and $^{13}$C NMR, respectively). All the NMR assignments are based on $^{1}$H and $^{13}$C spectra using $^{1}$H, $^{13}$C-HSQC and CIGAR-HMBC spectra, $^{1}$H, $^{1}$H-DQ-COSY and NOESY spectra, which allowed the unambiguous assignment of all NMR signals. Demycarosyl-3D-β-D-digitoxosyl-MTM (formula VIII) was furthermore studied by means of 1D-TOCSY spectra to separately identify the spin patterns of the sugars. The chemical structure of the compounds is shown in FIG. 4.

NMR and MS analysis of demycarosyl-3D-β-D-digitoxosyl-MTM (formula VIII), $C_{51}H_{74}O_{24}$. Negative ESI-MS m/z (relative intensity): 1069 (100) [M−H], 1105/1107 (22) [M+Cl$^-$], 939 (7) [M−H-Sugar 1A]. Positive ESI-MS m/z (relative intensity): 1093 (100) [M+Na], 1109 (11) [M+K], 833 (7) [M+H-{Sugar 1A and 1B}+Na], 811 (16) [M+H-Sugar 1A and 1B], 681 (14) [M+H-Trisaccharide], 421 (18) [M+H-Tri- and disaccharide]. HR-FAB m/z [M+Na$^+$]: calculated, 1093.4467; obtained, 1093.4447. UV/Vis (Methanol) λmax (ε): 412 (1532), 317 (1663), 279 (5112), 229 (5042) nm. IR (KBr) ν: 3420 (OH), 2920 (CH), 2848 (CH), 1716 (C=O), 1631 (C=O), 1514 (C=C), 1382, 1130, 1064 cm$^{-1}$. Table 1 shows the $^{1}$H-NMR and $^{13}$C-NMR data.

NMR and MS analysis of deoliosyl-3C-α-L-digitoxosyl-MTM (formula IX), $C_{52}H_{76}O_{24}$. Negative ESI-MS m/z (relative intensity): 1083 (100) [M−H], 1119/1121 (26) [M+Cl$^-$]. Positive ESI-MS m/z (relative intensity): 1107 (100) [M+Na$^+$], 1123 (13) [M+K$^+$], 847 (5) [M+H-{Disaccharide}+Na], 825 (27) [M+H-Disaccharide], 681 (11) [M+H-Trisaccharide], 551 (34) [M+H-Sugars 1A, 1B, 1D and 1E] and 421 (22) [M+H-Tri- and disaccharide]. HR-FAB m/z [M+Na$^+$]: calculated, 1107.4603; obtained, 1107.4624. UV/Vis (Methanol) λmax (ε): 412 (2148), 317 (2491), 278 (6851), 230 (6420) nm. IR (KBr) ν: 3409 (OH), 2924 (CH), 2850 (CH), 1716 (C=O), 1634 (C=O), 1514 (C=C), 1374, 1126, 1064 cm$^{-1}$. Table 2 shows the $^{1}$H-NMR and $^{13}$C-NMR data.

NMR and MS analysis of deoliosyl-3C-β-D-mycarosyl-MTM (formula X), $C_{46}H_{66}O_{21}$. Negative ESI-MS m/z (relative intensity): 953 (100) [M−H]. Positive ESI-MS m/z (relative intensity): 977 (100) [M+Na$^+$], 993 (5) [M+K$^+$], 695 (8) [M-Sugar 1A and 1B], 681 (10) [M-Sugar 1C and 1D] and 421 (20) [M+H-bis-disaccharide]. HR-FAB m/z [M+Na$^+$]: calculated, 977.3745; obtained, 977.3948. UV/Vis (Methanol) λmax (ε): 412 (1357), 316 (1629), 278 (3274), 230 (2982) nm. IR (KBr) ν: 3425 (OH), 2924 (CH), 2850 (CH), 1716 (C=O), 1631 (C=O), 1514 (C=C), 1374, 1122, 1064 cm$^{-1}$. Table 3 shows the $^{1}$H-NMR and $^{13}$C-NMR data.

NMR and MS analysis of 3A-deolivosyl-MTM (formula XI), $C_{46}H_{66}O_{21}$. Negative ESI-MS m/z (relative intensity): 953 (100) [M−H], 989/991 (9) [M+Cl$^-$], 823 (5) [M-Sugar 1B], 809 (8) [M+H-Sugar 1D]. Positive ESI-MS m/z (relative intensity): 955 (100) [M+Na$^+$], 993 (10) [M+K$^+$], 833 (13) [M+H-{Sugar 1D}+Na$^+$], 825 (11) [M+H-Sugar 1B], 695 (5) [M+H-Sugar 1A and 1B], 681 (25) [M+H-Sugar 1C and 1D], 551 (50) [M+H-Sugars 1A, 1B and 1D] and 421 (33) [M+H-Tri- and monosaccharide]. HR-FAB m/z [M+Na$^+$]: calculated, 977.3735; obtained, 977.3950. UV/Vis (Methanol) λmax (ε):412 (2178), 316 (2310), 278 (8099), 231 (7363) nm. IR (KBr) ν: 3421 (OH), 2924 (CH), 2850 (CH), 1716 (C=O), 1634 (C=O), 1514 (C=C), 1374, 1122, 1060 cm$^{-1}$. Table 4 shows the $^{1}$H-NMR and $^{13}$C-NMR data.

EXAMPLE 3

Obtaining the *Streptomyces argillaceus* (pFL845) Bacterial Strain

The strain *Streptomyces argillaceus* (pFL845) was generated by means of introducing plasmid pFL845 in *Streptomyces argillaceus*. The introduction of the plasmid was carried out by means of protoplast transformation, following standard procedures (Kieser et al., Practical *Streptomyces* genetics, The John Innes Foundation, Norwich, Great Britain, 2000). Plasmid pFL845 has been previously described, and contains a series of genes encoding the biosynthesis of nucleosidyl diphosphate (NDP)-D-amicetose (*Chem. Commun.* (*Camb*). 2005 Mar. 28; (12):1604-6). The strain *Streptomyces argillaceus* (pFL845) was deposited on 15 Nov. 2006 in the Colección Española de Cultivos Tipo (CECT) [Spanish Type Culture Collection], Universidad de Valencia, Campus de Burjassot, 46100 Burjassot (Valencia, Spain) with accession number CECT 3383.

EXAMPLE 4

Production of demycarosyl-MTM (formula XII) and 6-dediolivosyl-6-β-D-amicetosyl-MTM (formula XIII)

To purify the novel derivatives of mithramycin produced by *S. argillaceus* (pFL845), this strain was cultured in eight 2 L flasks containing 400 ml of R5A medium supplemented with thiostrepton (5 µg/ml f.c.). After 6 days of incubation at 30° C., the cultures were centrifuged, filtered and a solid-phase extraction was carried out. The extract was then subjected to a first chromatography using a µBondapak C18 cartridge. The elution was carried out at 10 ml/min using a mixture of acetonitrile and TFA in water (42:58) as a mobile phase. A second chromatography was then carried out in Symmetry C18 (7.8×300), at 3 ml/min using a mixture of acetonitrile and TFA in water (37:63, for 845-1 P1; 42:58, for 845-1 P3) as a mobile phase. The following yield was obtained: 16.1 mg of demycarosyl-MTM (formula XII) and 4.3 mg of 6-dediolivosyl-6-β-D-amicetosyl-MTM (formula XIII). The products were characterized by HPLC-MS, as described in Example 2.

NMR and MS analysis of demycarosyl-MTM (formula XII), $C_{45}H_{64}O_{21}$. Amorphous yellow solid. $[\alpha]^{25}_D$ −25 (c 0.032, MeOH); Negative ESI-MS m/z (relative intensity): 939 (100) [M−H], 975/977 (28) [M+Cl$^-$], 809 (10) [M−H−{sugar A}], 679 (5) [M−H−{Disaccharide}]. Positive ESI-MS m/z (relative intensity): 963 (100) [M+Na$^+$], 979 (10) [M+K$^+$], 833 (9) [M+H−{Sugar A}+Na$^+$], 811 (5) [M+H−sugar A], 681 (20) [M+H−{disaccharide}], 703 (8) [M+H−{Disaccharide}+Na], 421 (15) [M+H−{bis-disaccharide}]. HR-FAB m/z [M+Na$^+$]: calculated, 963.3804; obtained, 963.3793. UV/Vis (Methanol) λmax (ε): 430 (10,200), 316 (6400), 281 (50,400), 231 (11,000) nm. IR (KBr) v: 3421 (OH), 2924 (CH), 2850 (CH), 1716 (C=O), 1631 (C=O), 1514 (C=C), 1374, 1122, 1064 cm$^{-1}$. Table 5 shows the $^1$H-NMR and $^{13}$C-NMR data.

NMR and MS analysis of 6-dediolivosyl-6-β-D-amicetosyl-MTM (formula XIII), $C_{46}H_{66}O_{20}$. Amorphous yellow solid. $[\alpha]^{25}_D$ −22 (c 0.027, MeOH); Negative ESI-MS m/z (relative intensity): 937 (100) [M−H], 973/975 (23) [M+Cl$^-$], 823 (10) [M−H−{sugar A}]. Positive ESI-MS m/z (relative intensity): 961 (100) [M+Na$^+$], 977 (15) [M+K$^+$], 825 (10) [M+H−{sugar A}], 535 (9) [M+H−{Trisaccharide}], 421 (12) [M+H−{Tri- and monosaccharide}]. HR-FAB m/z [M+Na$^+$]: calculated, 961.4053; obtained, 961.4045. UV/Vis (Methanol) λmax (ε):430 (10,500), 316 (6,500), 281 (48,400), 230 (12,600). IR (KBr) v: 3425 (OH), 2928 (CH), 2850 (CH), 1716 (C=O), 1631 (C=O), 1514 (C=C), 1374, 1122, 1064 cm$^{-1}$. Table 6 shows the $^1$H-NMR and $^{13}$C-NMR data.

EXAMPLE 5

Obtaining the *Streptomyces argillaceus* (pFL942) Bacterial Strain

The strain *Streptomyces argillaceus* (pFL942) was generated by means of introducing plasmid pFL942 in *Streptomyces argillaceus*. The introduction of the plasmid was carried out by means of protoplast transformation, following standard procedures (Kieser et al., Practical *Streptomyces* genetics, The John Innes Foundation, Norwich, Great Britain, 2000). Plasmid pFL942 has been previously described, and contains a series of genes encoding the biosynthesis of nucleosidyl diphosphate (NDP)-L-mycarose (*Chemistry & Biology*. 2004, (11):1709-18). The strain *Streptomyces argillaceus* (pFL942) was deposited on May 2, 2008 in the Colección Española de Cultivos Tipo (CECT) [Spanish Type Culture Collection], Universidad de Valencia, Campus de Burjassot, 46100 Burjassot (Valencia, Spain) with accession number CECT 7368.

EXAMPLE 6

Production of deoliosyl-demycarosyl-3C-β-D-boivinosyl-MTM (formula XVII) and demycarosyl-3D-β-D-digitoxosyl-MTM (formula VIII)

To purify the novel derivatives of mithramycin produced by *S. argillaceus* (pFL942), this strain was cultured in R5A solid medium. 100 Agar plates were uniformly inoculated with spores and after 6 days of incubation at 28° C., the cultures were extracted 3 times with ethyl acetate. The extract was then subjected to a first chromatography using a µBondapak C18 radial compression cartridge. The elution was carried out at 10 ml/min using a mixture of acetonitrile and TFA in water (50:50) as a mobile phase. A second chromatography was then carried out in a Sunfire PrepC18 column (10×250 mm, Waters), at 7 ml/min using a mixture of acetonitrile and 0.1% TFA in water (37:63) as a mobile phase. The HPLC fractions were collected on 0.1M potassium phosphate buffer (pH=7) and after each purification, the samples were diluted 4 times with water, desalted, concentrated and lyophilized. The following yield was obtained: 3 mg of deoliosyl-demycarosyl-3C-β-D-boivinosyl-MTM (formula XVII) and 6.9 mg of demycarosyl-3D-β-D-digitoxosyl-MTM (formula VIII). The products were characterized by HPLC-MS, as described in Example 2. The compound demycarosyl-3D-β-D-digitoxosyl-MTM (formula VIII) is characterized in Example 2.

NMR and MS analysis of deoliosyl-demycarosyl-3C-β-D-boivinosyl-MTM (formula XVII), $C_{45}H_{64}O_{21}$. Amorphous yellow solid. $[\alpha]^{25}_D$ −22 (c 0.029, MeOH); Negative ESI-MS m/z (relative intensity): 939 (100) [M−H]. Positive ESI-MS m/z (relative intensity): 963 (100) [M+Na$^+$], 979 (10) [M+K$^+$], 833 (10) [M+Na$^+$−{Sugar A}], 703 (50) [M+H−{disaccharide}], 443 (12) [aglycon+Na$^+$]. HR-FAB m/z [M+Na$^+$]: calculated, 939.3849; obtained, 939.3867. UV/Vis (Methanol) λmax (ε):430 (10,600), 317 (6800), 281 (49,500), 230 (10,000) nm. IR (KBr) v: 3431 (OH), 2926 (CH), 2851 (CH), 1716 (C=O), 1631 (C=O), 1514 (C=C), 1374, 1121, 1064 cm$^{-1}$. Table 7 shows the $^1$H-NMR and $^{13}$C-NMR data.

EXAMPLE 7

Obtaining the Bacterial Strain *Streptomyces argillaceus* M7U1 (pFL845)

The strain *Streptomyces argillaceus* M7U1 (pFL845) was generated by means of introducing plasmid pFL845 in *Streptomyces argillaceus* M7U1. The introduction of the plasmid was carried out by means of protoplast transformation, following standard procedures (Kieser et al., Practical *Streptomyces* genetics, The John Innes Foundation, Norwich, Great Britain, 2000). The strain *Streptomyces argillaceus* M7U1 has been previously described (*Mol. Gene. Genet.* 2001, 264, 827-835). Plasmid pFL845 has been previously described, and contains a series of genes encoding the biosynthesis of nucleosidyl diphosphate (NDP)-D-D-amicetose (*Chem.*

*Commun. (Camb).* 2005 Mar. 28; (12):1604-6). The strain *Streptomyces argillaceus* M7U1 (pFL845) was deposited on May 2, 2008 in the Colección Española de Cultivos Tipo (CECT) [Spanish Type Culture Collection], Universidad de Valencia, Campus de Burjassot, 46100 Burjassot (Valencia, Spain) with accession number CECT 7369.

EXAMPLE 8

Production of 6-dediolivosyl-6-β-D-amicetosyl-deoliosyl-demycarosyl-3C-β-D-boivinosyl-MTM (formula XVIII); deoliosyl-demycarosyl-3C-β-D-olivosyl-3D-β-D-digitoxosyl-MTM (formula XIX); 6-dediolivosyl-6-β-D-amicetosyl-deoliosyl-demycarosyl-3C-β-D-olivosyl-3D-β-D-digitoxosyl-MTM (formula XX) and 6-dediolivosyl-6-β-D-amicetosyl-deoliosyl-3C-β-D-olivosyl-MTM (formula XXI)

To purify the novel derivatives of mithramycin produced by *S. argillaceus* M7U1 (pFL845), this strain was cultured in R5A solid medium. 100 Agar plates were uniformly inoculated with spores and after 6 days of incubation at 28° C., the cultures were extracted 3 times with ethyl acetate. The extract was then subjected to a first chromatography using a μBondapak C18 radial compression cartridge. The elution was carried out at 10 ml/min using a mixture of acetonitrile and TFA in water (50:50) as a mobile phase. A second chromatography was then carried out in a Sunfire PrepC18 column (10×250 mm, Waters), at 7 ml/min using a mixture of acetonitrile and 0.1% TFA in water (40:60) as a mobile phase. The HPLC fractions were collected on 0.1M potassium phosphate buffer (pH=7) and after each purification, the samples were diluted 4 times with water, desalted, concentrated and lyophilized. The following yield was obtained: 1.7 mg of 6-dediolivosyl-6-β-D-amicetosyl-deoliosyl-demycarosyl-3C-β-D-boivinosyl-MTM (formula XVIII), 6.7 mg of deoliosyl-demycarosyl-3C-β-D-olivosyl-3D-β-D-digitoxosyl-MTM (formula XIX), 12.2 mg of 6-dediolivosyl-6-β-D-amicetosyl-deoliosyl-demycarosyl-3C-β-D-olivosyl-3D-β-D-digitoxosyl-MTM (formula XX) and 17 mg of 6-dediolivosyl-6-β-D-amicetosyl-deoliosyl-3C-8-D-olivosyl-MTM (formula XXI). The products were characterized by HPLC-MS, as described in Example 2.

NMR and MS analysis of 6-dediolivosyl-6-β-D-amicetosyl-deoliosyl-demycarosyl-3C-β-D-boivinosyl-MTM (formula XVIII): $C_{39}H_{54}O_{17}$. Amorphous yellow solid. $[\alpha]^{25}_D$ −23 (c 0.026, MeOH); Negative ESI-MS m/z (relative intensity): 793 (10%) [M−H], 777 (100%) (M−H2O). Positive ESI-MS m/z (relative intensity): 795 (25) [M+H], 817 (20) [M+Na$^+$], 687 (100), [M+H-{sugar A}], 673 (11) [M+H{sugar A and 1C}], 443 (12) [aglycon+Na]. HR-FAB m/z [M+Na$^+$]: calculated, 817.3253; obtained, 817.3238. UV/Vis (Methanol) λmax (ε): 430 (10,800), 316 (6700), 280 (50,700), 231 (13,000) nm. IR (KBr) ν: 3428 (OH), 2925 (CH), 2850 (CH), 1716 (C=O), 1632 (C=O), 1514 (C=C), 1374, 1121, 1063 cm$^{-1}$. Table 8 shows the $^1$H-NMR and $^{13}$C-NMR data.

NMR and MS analysis of deoliosyl-demycarosyl-3C-β-D-olivosyl-3D-β-D-digitoxosyl-MTM (formula XIX), $C_{51}H_{74}O_{24}$. Amorphous yellow solid. $[\alpha]^{25}_D$ −21 (c 0.020, MeOH); Negative ESI-MS m/z (relative intensity): 1069 (20) [M−H]. Positive ESI-MS m/z (relative intensity): 1071 (48) [M+H], 1093 (26) [M+Na$^+$], 963 (28) [M+Na$^+$-{monosaccharide}], 833 (16)) [M+Na$^+$-{disaccharide}], 703 (12) [M+Na$^+$-{Trisaccharide}], 550 (14) [M+Na$^+$-{tetrasaccharide], 443 (26) [M+H-{Tri- and disaccharide}]. HR-FAB m/z [M+Na$^+$]: calculated, 1093.4462; obtained, 1093.4447. UV/Vis (Methanol) λmax (ε): 430 (10,600), 316 (6500), 280 (49,500), 231 (12,800) nm. IR (KBr) ν: 3423 (OH), 2921 (CH), 2850 (CH), 1716 (C=O), 1631 (C=O), 1514 (C=C), 1382, 1131, 1064 cm$^-$. Table 9 shows the $^1$H-NMR and $^{13}$C-NMR data.

NMR and MS analysis of 6-dediolivosyl-6-β-D-amicetosyl-deoliosyl-demycarosyl-3C-β-D-olivosyl-3D-β-D-digitoxosyl-MTM (formula XX), $C_{45}H_{62}O_{20}$. Amorphous yellow solid. $[\alpha]^{25}_D$ −15 (c 0.024, MeOH); Positive ESI-MS m/z (relative intensity): 947 (25) [M+Na$^+$], 817 (100) [M+Na$^+$-{sugar C}], 795 (12) [M+H-sugar C]. HR-FAB m/z [M+Na$^+$]: calculated, 947.3883; obtained, 947.3867. UV/Vis (Methanol) λmax (ε): 430 (10,400), 316 (6500), 281 (48,000), 232 (11,900) nm. IR (KBr) ν: 3426 (OH), 2928 (CH), 2843 (CH), 1716 (C=O), 1632 (C=O), 1514 (C=C), 1374, 1121, 1063 cm$^-$. Table 10 shows the $^1$H-NMR and $^{13}$C-NMR data.

NMR and MS analysis of 6-dediolivosyl-6-β-D-amicetosyl-deoliosyl-3C-β-D-olivosyl-MTM (formula XXI), $C_{45}H_{64}O_{21}$. Negative ESI-MS m/z (relative intensity): XXX. Positive ESI-MS m/z (relative intensity): XXX. HR-FAB m/z [M+Na$^+$]: calculated, 940.39; obtained, XXX. UV/Vis (Methanol) λmax (ε): XXX. IR (KBr) ν: XXX. Table 11 shows the $^1$H-NMR and $^{13}$C-NMR data.

EXAMPLE 9

Antitumor activity of demycarosyl-3D-β-D-digitoxosyl-MTM (formula VIII), deoliosyl-3C-α-L-digitoxosyl-MTM (formula IX), deoliosyl-3C-β-D-mycarosyl-MTM (formula X), 3A-deoliovosyl-MTM (formula XI), demycarosyl-MTM (formula XII), 6-dediolivosyl-6-β-D-amicetosyl-MTM (formula XIII)

deoliosyl-demycarosyl-3C-β-D-boivinosyl-MTM [formula (XVII)]; 6-dediolivosyl-6-β-D-amicetosyl-deoliosyl-demycarosyl-3C-β-D-boivinosyl-MTM [formula (XVIII)]; deoliosyl-demycarosyl-3C-β-D-olivosyl-3D-β-D-digitoxosyl-MTM [formula (XIX)]; 6-dediolivosyl-6-β-D-amicetosyl-deoliosyl-demycarosyl-3C-β-D-olivosyl-3D-β-D-digitoxosyl-MTM [formula (XX)], and 6-dediolivosyl-6-β-D-amicetosyl-deoliosyl-3C-β-D-olivosyl-MTM [formula (XXI)].

The derivatives of MTM were assayed against a series of cell lines from tumors. Cell growth and viability were quantitatively determined, using a colorimetric type assay, using the reaction with sulforhodamine B (SRB) according to the technique described by Faircloth et al. (*Journal of Tissue and Culture Methods* 1988, 11, 201-205). The results are shown in Table 5.

96-well microtiter plates were inoculated with cells (5×10$^3$ cells per well) in aliquots of 195 μl of medium, incubating them for 18 hours in medium without added compound, to allow the cells to adhere to the surface. The compounds to be assayed were then added, in 5 μl samples, in a concentration range from 10 to 10$^{-8}$ μg/ml, dissolved in DMSO/EtOH (0.2% in PS buffer). After 48 hours of exposure, the antitumor effect was measured using the SRB technique: the cells were fixed adding 50 μl of 50% (w/v) cold trichloroacetic acid and incubated for 60 minutes at 4° C. The plates were washed with deionized water and dried. 100 μl of SRB solution (0.4% w/v in 1% acetic acid) were added to each well, and incubated for 10 minutes at room temperature. The non-bound SRB was eliminated, washing with 1% acetic acid. The plates were air dried and the bound dye was dissolved with Tris buffer. Optical densities were read in an automatic plate spectrophotometer reader at a wavelength of 490 nm. Table 12 shows the results of $GI_{50}$ (growth inhibition). The six compounds assayed showed cytotoxic activity against the tumor cell lines assayed, demycarosyl-3D-β-D-digitoxosyl-MTM (formula VIII) being the most active (with an activity similar to that of MTM), and demycarosyl-MTM (formula XII) and 6-dediolivosyl-6-β-D-amicetosyl-MTM (formula XIII) being the least active.

TABLE 1

Figure 1:
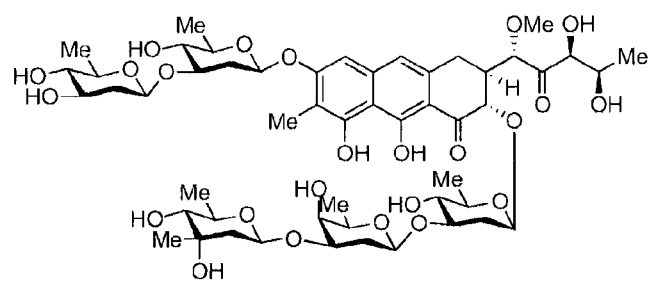
FIG. 1. Chemical structure of mithramycin.
Figure 2:
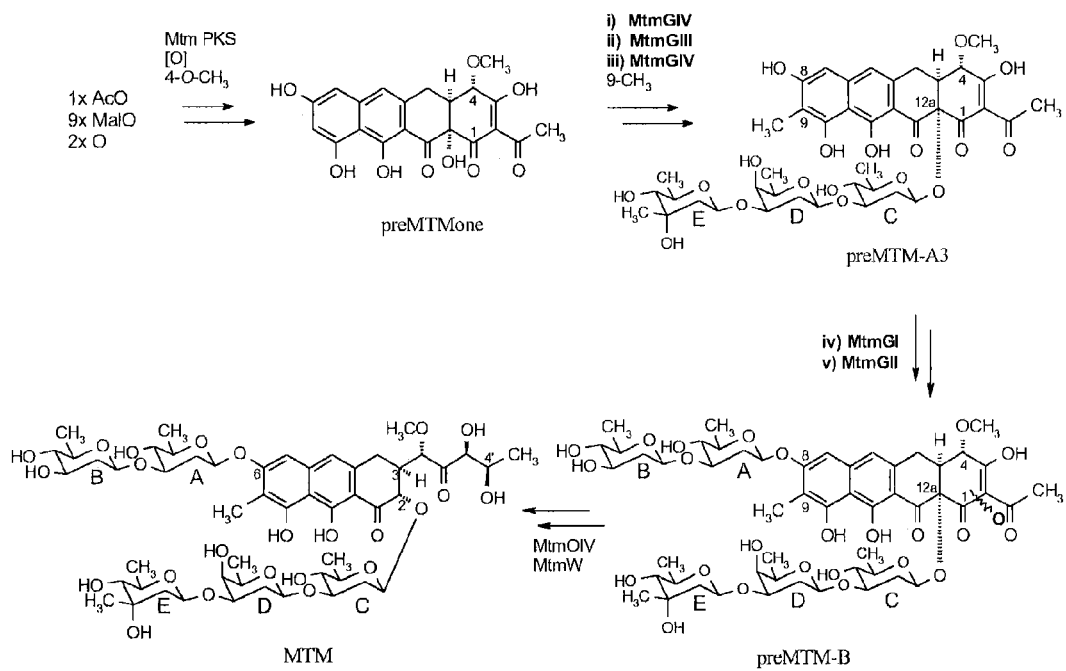
FIG. 2. Mithramycin biosynthesis. Abbreviations: AcO, acetate; MalO, malonate; Mtm PKS, mithramycin polyketide synthase; preMTMone, premithramycinone; preMTM-A3, premithramycin A3; preMTM-B, premithramycin B; MTM, mithramycin.
Figure 3A:
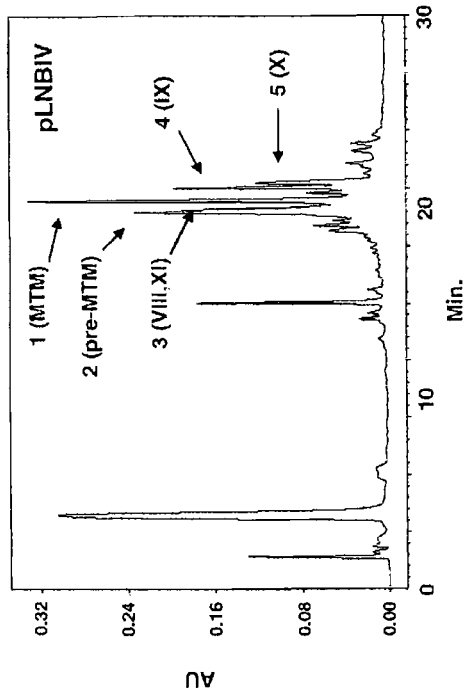
FIG. 3A. HPLC analysis of a *Streptomyces argillaceus* (pFL845) extract. Peak identifier: 1=mithramycin (MTM); 2=premithramycin A1 (preMTM); 3=demycarosyl-MTM [formula (XII)]; 4=6-dediolivosyl-6-β-D-amicetosyl-MTM [formula (XIII)]
Figure 3B:
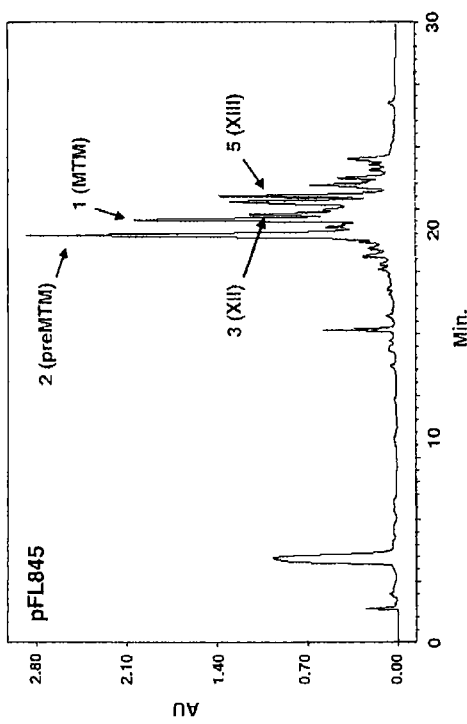
FIG. 3B. HPLC analysis of a *Streptomyces argillaceus* (pLNBIV) extract. Peak identifier: 1=mithramycin (MTM); 2=premithramycin A1 (preMTM); 3=demycarosyl-MTM [formula (XII)], 3A-deolivosyl-MTM (XI), and demycarosyl-3D-β-D-digitoxosyl-MTM [formula (VIII)]; 4=deoliosyl-3C-α-L-digitoxosyl-MTM [formula (IX)]; 5=deoliosyl-3C-β-D-mycarosyl-MTM [formula (X)].
Figure 3C:
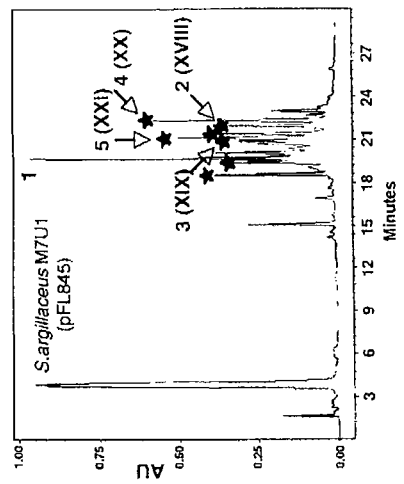
FIG. 3C. HPLC Analysis of a *Streptomyces argillaceus* (pFL942) extract. Peak identifier: 1=mithramycin (MTM); 2=demycarosyl-3D-β-D-digitoxosyl-MTM [formula (VIII)]; 3=deoliosyl-demycarosyl-3C-β-D-boivinosyl-MTM [formula (XVII)]
Figure 3D:
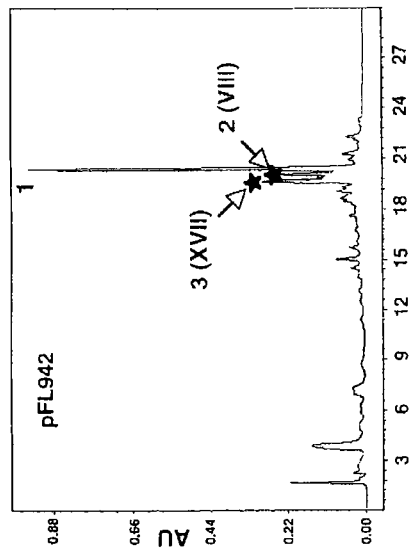
FIG. 3D. HPLC analysis of a *Streptomyces argillaceus* M7U1 (pFL845) extract. Peak identifier: 1=premithramycin A1 (preMTM); 2=6-dediolivosyl-6-β-D-amicetosyl-deoliosyl-demycarosyl-3C-β-D-boivinosyl-MTM [formula (XVIII)]; 3=deoliosyl-demycarosyl-3C-β-D-olivosyl-3D-β-D-digitoxosyl-MTM [formula (XIX)]; 4=6-dediolivosyl-6-β-D-amicetosyl-deoliosyl-demycarosyl-3C-β-D-olivosyl-3D-β-D-digitoxosyl-MTM [formula (XX)]; 5=6-dediolivosyl-6-β-D-amicetosyl-deoliosyl-3C-β-D-olivosyl-MTM [formula (XXI)].

$^1$H- and $^{13}$C-NMR data of demycarosyl-3D-β-D-digitoxosyl-MTM [formula (VIII)] (Pyridine-$d_5$, 400 MHz).

| C | $^1$H-NMR δ (J in Hz) | $^{13}$C-NMR (δ) | Multiplicity | HMBC | NOESY |
|---|---|---|---|---|---|
| 1 | — | 204.3 | C | | |
| 2 | 4.96 (d, J = 11.6 Hz) | 78.7 | CH | C-1, C-1(A*), C-3, C-4, C-1' | H-1(C*), H-3, H-4α, H-4e |
| 3 | 3.48 (m) | 42.8 | CH | C-2, C-4, C-1' | H-2, H-4a, H-4e, H-1' |
| 4a | 3.11 (dd, J = 15.9 and 3.6 Hz) | 28.5 | $CH_2$ | C-2, C-3, C-1' | H-3, H-2 |
| 4e | 3.27 (dd, J = 15.9 and 13.0 Hz) | | | | H-3, H-2 |
| 4a | — | 137.2 | C | | |
| 5 | 7.05 (s) | 102.2 | CH | C-6, C-8a, C-7, C-10 | |
| 6 | — | 160.4 | C | | H-10, H-1(A*), H-5(A*) |
| 7 | — | 111.7 | C | | |
| 7-$CH_3$ | 2.47 (s) | 9.4 | $CH_3$ | C-6, C-7, C-8 | |
| 8 | — | 156.9 | C | | |
| 8a | — | 109.4 | C | | |
| 9 | — | 165.7 | C | | |
| 9a | — | 108.9 | C | | |
| 10 | 6.63 (s) | 117.4 | CH | C-5, C-5a, C-8a, C-9a | H-5, H-1(A*), H-4a, H-4e |
| 10a | — | 139.5 | C | | |
| 1' | 5.49 (d, J = 1.2 Hz) | 83.1 | CH | C-2, C-3, C-4, C-1'-Me, C-2' | H-2, H-3, H-1'(Me) |
| 1'-$CH_3$ | 3.69 (s) | 59.1 | | C-1', C-2', C-3 | |
| 2' | — | 213.5 | C | | |
| 3' | 4.70 (d, J = 2.8 Hz) | 81.4 | CH | C-2', C-4', C-5' | H-4', H-5' |
| 4' | 4.84 (dq, J = 6.2 and 2.8 Hz) | 69.6 | CH | C-2', C-3', C-5' | H-5', H-3' |
| 5' | 1.60 (d, J = 6.2 Hz) | 19.7 | $CH_3$ | C-3', C-4' | H-4'-H-3' |
| 1A | 5.68 (dd, J = 9.6 and 2.0 Hz) | 97.9 | CH | C-6 | H-3(A*), H-5(A*), H-2a(A*), H-2e(A*), H-5, H-10 |
| 2αA | 2.25 (ddd, J = 12, 12 and 9.6 Hz) | 38.0 | $CH_2$ | C-1(A*), C-3(A*), C-4(A*) | H-1(A*), H-4((A*) |
| 2eA | 2.72 (ddd, J = 12, 5.0 and 2.0 Hz) | | | | H-1(A*), H-3(A*), H-2α(A*) |
| 3A | 4.29 (ddd, J = 12, 9.0 and 5.0 Hz) | 80.1 | $CH_2$ | C-1(B*), C-4(A*) | H-1(A*), H-1(B*)H-5(A*), H-2α(A*), H-2e(A*) |
| 4A | 3.63 (t, J = 9.0 Hz) | 76.1 | CH | C-3(A*), C-5(A*), C-6(A*) | H-2α(A*), H$_3$-6(A*) |
| 5A | 4.00 (dq, J = 9.0 and 6.0 Hz) | 73.9 | CH | C-1(A*), C-3(A*), C-4(A*), C-6(A*) | H-1(A*), H-3(A*), H$_3$-6(A*) |
| 6A | 1.71 (d, J = 6.0 Hz) | 19.4 | $CH_3$ | C-4(A*), C-5(A*) | H-4(A*), H-5(A*) |
| 1B | 5.05 (dd, J = 9.6 and 2.0 Hz) | 99.4 | CH | C-3(A*), | H-2α(B*), 2e(B*)H-3(A*), H-3(B*), H-5(B*) |
| 2αB | 2.15 (ddd, J = 12, 12 and 9.6 Hz) | 41.6 | $CH_2$ | C-1(B*), C-3(B*), C-4(B*) | H-1(B*), H-4(B*) |
| 2eB | 2.65 (ddd, J = 12, 5.0 and 2.0 Hz) | | | | H-1(B*) |
| 3B | 4.16 (ddd, J = 12, 9.0 and 5.0 Hz) | 72.4 | CH | C-4(B*) | H-2a(B*), H-2e(B*), H-1(B*), H-5(B*) |

TABLE 1-continued $^1$H- and $^{13}$C-NMR data of demycarosyl-3D-β-D-digitoxosyl-MTM [formula (VIII)] (Pyridine-d$_5$, 400 MHz).

| C | $^1$H-NMR δ (J in Hz) | $^{13}$C-NMR (δ) | Multiplicity | HMBC | NOESY |
|---|---|---|---|---|---|
| 4B | 3.58 (t, J = 9.0 Hz) | 78.7 | CH | C-3(B*), C-5(B*), C-6(B*) | H-2α(B*), H$_3$-6(B*) |
| 5B | 3.75 (dq, J = 9.0 and 6.0 Hz) | 74.6 | CH | C-1(B*), C-3(B*), C-4(B*), C-6(B*) | H-1(B*), H-3(B*), H$_3$-6 (B*) |
| 6B | 1.64 (d, J = 6.0 Hz) | 19.1 | CH$_3$ | C-4(B*), C-5(B*) | H-5(B*) |
| 1C | 5.39 (dd, J = 9.6 and 2.0 Hz) | 101.9 | CH | C-2 | H-2, H-3(C*), H-5(C*), H-2e(C*) |
| 2αC | 2.02 (ddd, J = 12, 12 and 9.6 Hz) | 38.7 | CH$_2$ | C-1(C*), C-3(C*), C-4(C*) | H-4(C*) |
| 2eC | 2.99 (ddd, J = 12, 5.0 and 2.0 Hz) | | | | H-1(C*) |
| 3C | 4.06 (ddd, J = 12, 9.0 and 5.0 Hz) | 81.7 | CH | C-1(D*), C-4(C*) | H-1(C*), H-1(D*), H-5(C*), H-2e(C*) |
| 4C | 3.46 (t, J = 9.0 Hz) | 76.3 | CH | C-3(C*), C-5(C*), C-6(C*) | H-2α(C*), H$_3$-6(C*) |
| 5C | 3.68 (dq, J = 9.0 and 6.0 Hz) | 73.5 | CH | C-4(C*), C-6(C*) | H-3(C*), H-1(C*), H$_3$-6(C*) |
| 6C | 1.59 (d, J = 6.0 Hz) | 19.7 | CH$_3$ | C-4(C*), C-5(C*) | H-5(C*), H-4(C*) |
| 1D | 4.78 (dd, J = 9.6 and 2.0 Hz) | 100.4 | CH | C-3(C*) | H-3(D*), H-5(D*), H-2e(D*), H-3(C*) |
| 2αD | 2.42 (ddd, J = 12, 12 and 9.6 Hz) | 33.3 | CH$_2$ | C-1(D*), C-3(D*), C-4(D*) | H-1(D*) |
| 2eD | 2.18 (ddd, J = 12, 5.0 and 2.0 Hz) | | | | |
| 3D | 4.22 (ddd, J = 12, 5.0 and 2.5 Hz) | 77.2 | CH | C-1(E*), C-4(D*) | H-1(D*), H-2e(D*), H-5(D*), H-1(E*) |
| 4D | 4.10 (brd, J = 2.5 Hz) | 70.2 | CH | C-3(D*), C-5(D*) | H$_3$-6(D*) |
| 5D | 3.71 (dq, J = 6.0 and 2.5 Hz) | 74.6 | CH | C-4(D*), C-6(D*) | H-1(D*), H-3(D*), H$_3$-6(D*) |
| 6D | 1.54 (d, J = 6.0 Hz) | 19.4 | CH$_3$ | C-4(D*), C-5(D*) | H-5(D*) |
| 1E | 5.62 (dd, J = 9.6 and 2.0 Hz) | 97.8 | CH | C-3(D*) | H-5(E*), H-2α(E*)H-2e(E*), H-3(D*) |
| 2αE | 2.00 (ddd, J = 12, 9.6 and 3.0 Hz) | 40.3 | CH$_2$ | C-1(E*), C-3(E*), C-4(E*) | H-1(E*), H-2α(E*) |
| 2e-E | 2.45 (ddd, J = 12, 3.0 and 2.0 Hz) | | | | |
| 3E | 4.45 (ddd, J = 3.0, 3.0, and 3.0 Hz) | 69.1 | CH | C-4(E*) | H-4(E*) |
| 4E | 3.62 (dd, J = 9.2 and 3.0 Hz) | 72.4 | CH | C-3(E*), C-5(E*) | H-2α(E*), H-3(E*), H$_3$-6(E*) |
| 5E | 4.42 (dq, J = 9.2 and 6.0 Hz) | 71.2 | CH | C-1(E*), C-4(E*), C-6(E*) | H$_3$-6(E*), H-1(E*) |
| 6E | 1.61 (d, J = 6.0 Hz) | 17.9 | CH$_3$ | C-4(E*), C-5(E*) | H-5(E*) |

*A = B = C = D = E: sugars

TABLE 2

$^1$H- and $^{13}$C-NMR data of deoliosyl-3C-α-L-digitoxosyl-MTM [formula (IX)] (Pyridine-d$_5$, 400 MHz).

| C | $^1$H-NMR δ (J in Hz) | $^{13}$C-NMR (δ) | C | HMBC | NOESY |
|---|---|---|---|---|---|
| 1 | — | 204.2 | C | | |
| 2 | 4.93 (d, J = 11.6 Hz) | 77.9 | CH | C-1, C-1(A*), C-3, C-4, C-1' | H-1(C*), H-3, H-4a, H-4e |
| 3 | 3.41 (m) | 42.8 | C | C-2, C-4, C-1' | H-2, H-4a, H-4e, H-1' |
| 4a | 3.08 (dd, J = 15.9 and 3.6 Hz) | 28.2 | CH$_2$ | C-2, C-3, C-1' | H-3, H-2 |
| 4e | 3.26 (dd, J = 15.9 and 13.0 Hz) | | | | H-3, H-2 |
| 4a | — | 137.2 | C | | |
| 5 | 7.04 (s) | 102.1 | CH | C-6, C-8a, C-7, C-10 | |
| 6 | — | 160.4 | C | | H-10, H-1(A*), H-5(A*) |
| 7 | — | 111.6 | C | | |
| 7-CH$_3$ | 2.47 (s) | 9.4 | CH$_3$ | C-6, C-7, C-8 | |
| 8 | — | 157.0 | C | | |
| 8a | — | 109.4 | C | | |
| 9 | — | 165.7 | C | | |
| 9a | — | 108.9 | C | | |
| 10 | 6.61 (s) | 117.4 | CH | C-5, C-5a, C-8a, C-9a | H-5, H-1(A*), H-4a, H-4e |
| 10a | — | 139.4 | C | | |
| 1' | 5.46 (d, J = 1.2 Hz) | 83.1 | CH | C-2, C-3, C-4, C-1'-CH$_3$, C-2' | H-2, H-3, H-1'(Me) |
| 1'-CH$_3$ | 3.69 (s) | 59.4 | CH$_3$ | C-1', C-2', C-3 | |
| 2' | — | 213.4 | C | | |
| 3' | 4.71 (d, J = 2.8 Hz) | 81.3 | CH | C-2', C-4', C-5' | H-4', H-5' |
| 4' | 4.84 (dq, J = 6.2 and 2.8 Hz) | 69.6 | CH | C-2', C-3', C-5' | H-5', H-3' |
| 5' | 1.58 (d, J = 6.2 Hz) | 21.1 | CH$_3$ | C-3', C-4' | H-4'-H-3' |
| 1A | 5.67 (dd, J = 9.6 and 2.0 Hz) | 97.9 | CH | C-6 | H-5, H-10, H-3(A*), H-5(A*), H-2α(A*), H-2e(A*) |
| 2αA | 2.24 (ddd, J = 12, 12 and 9.6 Hz) | 37.7 | CH$_2$ | C-1(A*), C-3(A*) | H-1(A*), H-4(A*) |
| 2eA | 2.73 (ddd, J = 12, 5.0 and 2.0 Hz) | | | | H-1(A*) |
| 3A | 4.29 (ddd, J = 12, 9.0 and 5.0 Hz) | 80.1 | CH$_2$ | C-1(B*), C-4(A*) | H-1(A*), H-1(B*), H-5(A*), H-2e(A*) |
| 4A | 3.63 (t, J = 9.0 Hz) | 76.1 | CH | C-3(A*), C-5(A*), C-6(A*) | H-2α(A*), H$_3$-6(A*) |
| 5A | 4.00 (dq, J = 9.0 and 6.0 Hz) | 73.9 | CH | C-4(A*), C-6(A*) | H-1(A*), H-3(A*), H-4(A*), H$_3$-6(A*) |
| 6A | 1.71 (d, J = 6.0 Hz) | 19.6 | CH$_3$ | C-4(A*), C-5(A*) | H-4(A*), H-5(A*), |
| 1B | 5.05 (dd, J = 9.6 and 2.0 Hz) | 99.3 | CH | C-3(A*) | H-3(A*), H-3(B*), H-5(B*), H-2α(B*), 2e(B*) |
| 2αB | 2.17 (ddd, J = 12, 12 and 9.6 Hz) | 41.6 | CH$_2$ | C-1(B*), C-3(B*) | H-1(B*), H-4(B*) |

TABLE 2-continued $^1$H- and $^{13}$C-NMR data of deoliosyl-3C-α-L-digitoxosyl-MTM [formula (IX)] (Pyridine-d$_5$, 400 MHz).

| C | $^1$H-NMR δ (J in Hz) | $^{13}$C-NMR (δ) | C | HMBC | NOESY |
|---|---|---|---|---|---|
| 2eB | 2.65 (ddd, J = 12, 5.0 and 2.0 Hz) | | | | H-1(B*) |
| 3B | 4.15 (ddd, J = 12, 9.0 and 5.0 Hz) | 72.4 | CH | C-1(B*), C-4(B*) | H-1(B*), H-4(B*), H-5(B*), |
| 4B | 3.58 (t, J = 9.0 Hz) | 78.7 | CH | C-3(B*), C-5(B*), C-6(B*) | H-2α(B*), H-3(B*), H-5(B*), H$_3$-6(B*) |
| 5B | 3.75 (dq, J = 9.0 and 6.2 Hz) | 74.0 | CH | C-4(B*), C-6(B*) | H-1(B*), H-3(B*), H-4(B*), H$_3$-6(B*), |
| 6B | 1.64 (d, J = 6.2 Hz) | 19.3 | CH$_3$ | C-4(B*), C-5(B*) | H-4(B*), H-5(B*) |
| 1C | 5.37 (dd, J = 9.6 and 2.0 Hz) | 101.9 | CH | C-2 | H-2, H-3(C*), H-5(C*), H-2e(C*), H-2α(C*) |
| 2αC | 1.93 (ddd, J = 12, 12 and 9.6 Hz) | 37.7 | CH$_2$ | C-3(C*) | H-4(C*) |
| 2eC | 2.98 (ddd, J = 12, 5.0 and 2.0 Hz) | | | | H-1(C*), H-1(D*), H-3(C*), H-2α(C*) |
| 3C | 4.08 (ddd, J = 12, 9.0 and 5.0 Hz) | 77.9 | CH | C-1(D*), C-4(C*) | H-1(C*), H-5(C*), H-4(C*), H-2e(C*) |
| 4C | 3.48 (t, J = 9.0 Hz) | 76.5 | CH | C-3(C*), C-6(C*) | H-2α(C*), H-5(C*), H-6(C*) |
| 5C | 3.68 (dq, J = 9.0 and 6.0 Hz) | 73.4 | CH | C-4(C*), C-6(C*) | H-1(C*), H-3(C*), H-4(C*) H$_3$-6(C*) |
| 6C | 1.57 (d, J = 6.0 Hz) | 19.4 | CH$_3$ | C-4(C*), C-5(C*) | H-4(C*), H-5(C*) |
| 1D | 5.22 (dd, J = 4.0 and 2.3 Hz) | 94.89 | CH | C-3(C*) | H-3(D*), H-2e(C*), H-2e(D*), H-2α(D*) |
| 2αD | 2.02 (ddd, J = 14.4, 4.0 and 3.0 Hz) | 34.6 | CH$_2$ | C-1(D*), C-3(D*) | H-1(D*), H-3(D*), H-2e(D*) |
| 2eD | 2.35(ddd, J = 14.4, 3.0 and 2.0 Hz) | | | | H-1(D*), H-3(D*), H-2α(D*) |
| 3D | 4.39 (ddd, J = 3.0, 3.0 and 3.0 Hz) | 75.2 | CH | C-1(D*), C-4(D*), C-5(D*) | H-1(D*), H-2α(D*), H-2e(D*) |
| 4D | 3.67 (dd, J = 9.0 and 3.0 Hz) | 72.8 | CH | C-5(D*), C-6(D*), C-1(E*) | H-5(D*), H$_3$-6(D*), H-1(E*), |
| 5D | 4.69 (dq, J = 9.0 and 6.2 Hz) | 67.4 | CH | C-4(D*), C-6(D*) | H-1(D*), H-4(D*), H$_3$-6(D*) |
| 6D | 1.54 (d, J = 6.2 Hz) | 18.9 | CH$_3$ | C-4(D*), C-5(D*) | H-4(D*), H-5(D*) |
| 1E | 5.44 (dd, J = 9.6 and 2.0 Hz) | 98.7 | CH | C-4(D*) | H-2α(E*), H-2e(E*), H-4(D*), H-5(E*) |
| 2αE | 1.86 (dd, J = 13.0, and 9.0 Hz) | 45.5 | CH$_2$ | C-1(E*), C-3(E*) | H-1(E*), H-4(E*) |
| 2eE | 2.41 (dd, J = 13.0 and 2.0 Hz) | | | | H-1(E*) |
| 3E | — | 71.4 | CH | | |
| 4E | 3.31 (d, J = 9.2 Hz) | 77.8 | CH | C-3(E*)Me, C-5(E*), C-6(E*) | H-2α(E*), H$_3$-3(E*), H-5(E*), H$_3$-6(E*) |
| 5E | 4.22 (dq, J = 9.2 and 6.0 Hz) | 72.2 | CH | | H-5(E*), H$_3$-6(E*) |
| 6E | 1.60 (d, J = 6.0 Hz) | 19.1 | CH$_3$ | C-4(E*), C-5(E*) | H-4(E*), H-5(E*) |
| 3E-Me | 1.44 (s) | 28.2 | CH$_3$ | C-3(E*), C-4(E*), C-2(E*) | H-4(E*) |

*A = B = C = D = E: sugars

TABLE 3

$^1$H- and $^{13}$C-NMR data of deoliosyl-3C-β-D-mycarosyl-MTM [formula (X)] (Pyridine-d$_5$, 400 MHz).

| C | $^1$H-NMR δ (J in Hz) | $^{13}$C-NMR (δ) | Multiplicity | HMBC | NOESY |
|---|---|---|---|---|---|
| 1 | — | 204.2 | C | | |
| 2 | 4.96 (d, J = 11.6 Hz) | 77.9 | CH | C-1, C-1(A*), C-3, C-4, C-1' | H-1(C*), H-3, H-4a, H-4e |
| 3 | 3.48 (m) | 42.6 | C | C-2, C-4, C-1' | H-2, H-4a, H-4e, H-1' |
| 4a | 3.10 (dd, J = 15.9 and 3.6 Hz) | 28.2 | CH$_2$ | C-2, C-3, C-1' | H-3, H-2 |
| 4e | 3.27 (dd, J = 15.9 and 13.0 Hz) | | | | H-3, H-2 |
| 4a | — | 137.2 | C | | |
| 5 | 7.04 (s) | 102.2 | CH | C-6, C-8a, C-7, C-10 | |
| 6 | — | 160.5 | C | | H-10, H-1(A*), H-5(A*) |
| 7 | — | 111.2 | C | | |
| 7-CH$_3$ | 2.47 (s) | 8.9 | CH$_3$ | C-6, C-7, C-8 | |
| 8 | — | 157.0 | C | | |
| 8a | — | 109.3 | C | | |
| 9 | — | 166.0 | C | | |
| 9a | — | 108.2 | C | | |
| 10 | 6.62 (s) | 117.4 | CH | C-5, C-5a, C-8a, C-9a | H-5, H-1(A*), H-4a, H-4e |
| 10a | — | 139.4 | C | | |
| 1' | 5.49 (d, J = 1.2 Hz) | 83.0 | CH | C-2, C-3, C-4, C-1'-CH$_3$, C-2' | H-2, H-3, H-1'(Me) |
| 1'-CH$_3$ | 3.71 (s) | 59.1 | | C-1', C-2', C-3 | |
| 2' | — | 213.2 | C | | |
| 3' | 4.71 (d, J = 2.8 Hz) | 81.0 | CH | C-2', C-4', C-5' | H-4', H-5' |
| 4' | 4.84 (dq, J = 6.2 and 2.8 Hz) | 69.3 | CH | C-2', C-3', C-5' | H-5', H-3' |
| 5' | 1.60 (d, J = 6.2 Hz) | 20.7 | CH$_3$ | C-3', C-4' | H-4'-H-3' |
| 1A | 5.67 (dd, J = 9.6 and 2.0 Hz) | 97.9 | CH | C-6 | H-5, H-5(A*), H-3(A*), H-2e(A*), H-10 |
| 2αA | 2.25 (ddd, J = 12, 12 and 9.6 Hz) | 37.6 | CH$_2$ | C-1(A*), C-3(A*) | H-4(A*), |
| 2eA | 2.72 (ddd, J = 12, 5.0 and 2.0 Hz) | | | | H-1(A*) |
| 3A | 4.28 (ddd, J = 12, 9.0 and 5.0 Hz) | 80.0 | CH$_2$ | C-1(B*), C-4(A*) | H-1(A*), H-1(B*), H-5(A*) |
| 4A | 3.63 (t, J = 9.0 Hz) | 75.9 | CH | C-3(A*), C-5(A*), C-6(A*) | H-2α(A*), H$_3$-6(A*) |
| 5A | 3.99 (dq, J = 9.0 and 6.0 Hz) | 73.8 | CH | C-4(A*), C-6(A*) | H-1(A*), H-3(A*), H$_3$-6(A*) |
| 6A | 1.71 (d, J = 6.0 Hz) | 19.0 | CH$_3$ | C-5(A*), C-4(A*) | H-4(A*), H-5(A*) |
| 1B | 5.05 (dd, J = 9.6 and 2.0 Hz) | 99.4 | CH | C-3(A*) | H-3(B*), H-3(A*), H-2e(B*), H-5(B*) |
| 2αB | 2.17 (ddd, J = 12, 12 and 9.6 Hz) | 41.2 | CH$_2$ | C-1(B*), C-3(B*) | H-1(B*), H-4(B*) |
| 2eB | 2.65 (ddd, J = 12, 5.0 and 2.0 Hz) | | | | H-1(B*) |
| 3B | 4.14 (ddd, J = 12, 9.0 and 5.0 Hz) | 72.1 | CH | C-4(B*) | H-3(A*), H-1(B*), H-5(B*) |
| 4B | 3.58 (t, J = 9.0 Hz) | 78.5 | CH | C-5(B*), C-6(B*) | H-2α(B*) |

TABLE 3-continued $^1$H- and $^{13}$C-NMR data of deoliosyl-3C-β-D-mycarosyl-MTM [formula (X)] (Pyridine-d$_5$, 400 MHz).

| C | $^1$H-NMR δ (J in Hz) | $^{13}$C-NMR (δ) | Multiplicity | HMBC | NOESY |
|---|---|---|---|---|---|
| 5B | 3.75 (dq, J = 9.0 and 6.0 Hz) | 73.7 | CH | C-4(B*), C-6(B*) | H-1(B*), H-3(B*), H$_3$-6(B*) |
| 6B | 1.64 (d, J = 6.0 Hz) | 18.9 | CH$_3$ | C-4(B*), C-5(B*) | H-5(B*) |
| 1C | 5.40 (dd, J = 9.6 and 2.0 Hz) | 101.6 | CH | C-2 | H-2, H-3(C*), H-5(C*), H-2e(C*) |
| 2αC | 2.02 (ddd, J = 12, 12 and 9.6 Hz) | 38.5 | CH$_2$ | C-3(C*) | H-4(C*) |
| 2eC | 2.99 (ddd, J = 12, 5.0 and 2.0 Hz) | | | | |
| 3C | 4.03 (ddd, J = 12, 9.0 and 5.0 Hz) | 81.1 | CH | C-1(D*), C-4(C*) | H-1(C*), H-1(D*), H-5(C*), H-2e(C*) |
| 4C | 3.48 (t, J = 9.0 Hz) | 76.3 | CH | C-3(C*), C-5(C*) | H-2α(C*), H$_3$-6(C*) |
| 5C | 3.69 (dq, J = 9.0 and 6.0 Hz) | 73.6 | CH | C-4(C*), C-6(C*) | H-3(C*), H-1(C*), H$_3$-6(C*) |
| 6C | 1.58 (d, J = 6.0 Hz) | 18.7 | CH$_3$ | C-4(C*), C-5(C*) | H-4(C*), H-5(C*) |
| 1D | 5.46 (dd, J = 9.6 and 2.0 Hz) | 98.9 | CH | C-3(C*) | H-3(C*), H-5(D*) |
| 2αD | 1.86 (dd, J = 13.0 and 9.6 Hz) | 45.2 | CH$_2$ | C-1(D*), C-3(D*), | H-2e(D*) |
| 2eD | 2.33 (dd, J = 13.0 and 2.0 Hz) | | | | |
| 3D | — | 71.2 | CH | | H-4(D*) |
| 4D | 3.35 (d, J = 9.2 Hz) | 77.4 | CH | C-3(D*), C-5(D*) | |
| 5D | 4.29 (dq, J = 9.2 and 6.2 Hz) | 72.1 | CH | C-4(D*), C-6(D*) | H-1(D*) |
| 6D | 1.61 (d, J = 6.2 Hz) | 19.0 | CH$_3$ | C-4(D*), C-5(D*) | H-5(D*), H-3D-Me |
| 3D-Me | 1.50 | 27.9 | CH$_3$ | C-2(D*), C-4(D*), C-3(D*) | H-4(D*) |

*A = B = C = D: sugars

TABLE 4

$^1$H- and $^{13}$C-NMR data of 3A-deolivosyl-MTM [formula (XI)] (Pyridine-d$_5$, 400 MHz).

| C | $^1$H-NMR δ (J in Hz) | $^{13}$C-NMR (δ) | C | HMBC | NOESY |
|---|---|---|---|---|---|
| 1 | — | 204.4 | C | — | |
| 2 | 4.96 (d, J = 11.6 Hz) | 77.9 | CH | C-1, C-1(A*), C-3, C-4, C-1' | H-1(C*), H-3, H-4a, H-4e |
| 3 | 3.48 (m) | 42.6 | C | C-2, C-4, C-1' | H-2, H-4a, H-4e, H-1' |
| 4a | 3.12 (dd, J = 15.9 and 3.6 Hz) | 28.1 | CH$_2$ | C-2, C-3, C-1' | H-3, H-2 |
| 4e | 3.26 (dd, J = 15.9 and 13.0 Hz) | | | | H-3, H-2 |
| 4a | — | 137.2 | C | | |
| 5 | 7.04 (s) | 102.2 | CH | C-6, C-8a, C-7, C-10 | |
| 6 | — | 160.6 | C | | H-10, H-1(A*), H-5(A*) |
| 7 | — | 111.7 | C | | |
| 7-CH$_3$ | 2.48 (s) | 8.9 | CH$_3$ | C-6, C-7, C-8 | |
| 8 | — | 157.0 | C | | |
| 8a | — | 109.4 | C | | |
| 9 | — | 165.9 | C | | |
| 9a | — | 108.9 | C | | |
| 10 | 6.62 (s) | 117.4 | CH | C-5, C-5a, C-8a, C-9a | H-5, H-1(A*), H-4a, H-4e |
| 10a | — | 139.5 | C | | |
| 1' | 5.49 (d, J = 1.2 Hz) | 83.0 | CH | C-2, C-3, C-4, C-1'-CH$_3$, C-2' | H-2, H-3, H-1'(Me) |
| 1'-CH$_3$ | 3.69 (s) | 59.1 | | C-1', C-2', C-3 | |
| 2' | — | 213.5 | C | | |
| 3' | 4.70 (d, J = 2.8 Hz) | 81.1 | CH | C-2', C-4', C-5' | H-4', H-5' |
| 4' | 4.84 (dq, J = 6.0 and 2.8 Hz) | 69.4 | CH | C-2', C-3', C-5' | H-5', H-3' |
| 5' | 1.59 (d, J = 6.0 Hz) | 20.7 | CH$_3$ | C-3', C-4' | H-4'-H-3' |
| 1A | 5.63 (dd, J = 9.6 and 2.0 Hz) | 98.0 | CH | C-6 | H-5, H-3(A*), H-(5*), H-2e(A*) |
| 2aA | 2.00 (ddd, J = 12.0, 12.0 and 9.6 Hz) | 36.7 | CH$_2$ | C-1(A*), C-3(A*), C-4(A*) | H-4(A*) |
| 2eA | 2.73 (ddd, J = 12.0, 5.0 and 2.0 Hz) | | | | H-1(A*) |
| 3A | 4.35 (ddd, J = 12, 9.2 and 5.0 Hz) | 74.2 | CH$_2$ | C-2(A*), C-4(A*) | H-1(A*), H-(5*) |
| 4A | 3.63 (t, 9.2) | 75.4 | CH | C-3(A*), C-5(A*), C-6(A*) | H-2a(A*), H$_3$-6(A*) |
| 5A | 4.01 (dq, J = 9.2 and 6.0 Hz) | 73.8 | CH | C-1(A*), C-3(A*), C-4(A*), C-6(A*) | H-1(A*), H-4(A*), H$_3$-6(A*) |
| 6A | 1.70 (d, J = 6.0 Hz) | 19.4 | CH$_3$ | C-4(A*), C-5(A*) | H-4(A*), H-5(A*) |
| 1B | 5.40 (dd, J = 9.6 and 2.0 Hz) | 101.7 | CH | C-2 | H-2, H-5(B*), H-3(B*), H-2e(B*) |
| 2aB | 2.02 (ddd, J = 12, 12 and 9.6 Hz) | 38.4 | CH$_2$ | C-1(B*), C-3(B*), C-4(B*) | H-4(B*) |
| 2eB | 2.99 (ddd, J = 12, 5.0 and 2.0 Hz) | | | | H-1(B*) |
| 3B | 4.06 (ddd, J = 12, 9.0 and 5.0 Hz) | 81.6 | CH | C-1(C*), C-4(B*) | H-1(B*), H-5(B*), H-1(C*) |
| 4B | 3.47 (t, J = 9.0 Hz) | 76.2 | CH | C-3(B*), C-5(B*), C-6(B*) | H-2a(B*), H$_3$-6(B*) |
| 5B | 3.67 (dq, J = 9.0 and 6.0 Hz) | 73.3 | CH | C-1(B*), C-4(B*), C-6(B*) | H-1(B*), H-3(B*), H$_3$-6(B*) |
| 6B | 1.60 (d, J = 6.0 Hz) | 18.9 | CH$_3$ | C-4(B*), C-5(B*) | H-5(B*) |
| 1C | 4.79 (dd, J = 9.6 and 2.0 Hz) | 100.3 | CH | C-3(B*) | H-3(B*), H-3(C*), H-5(C*) |
| 2aC | 2.42 (ddd, J = 12, 12 and 9.6 Hz) | 33.1 | CH$_2$ | C-1(C*), C-3(C*), C-4(C*) | |
| 2eC | 2.18 (ddd, J = 12, 5.0 and 2.0 Hz) | | | | |
| 3C | 4.21 (ddd, J = 12, 5.0 and 2.5 Hz) | 77.0 | CH | C-1(D*), C-4(C*) | H-1(C*), H-5(C*), H-1(D*) |
| 4C | 4.10 (brd, J = 2.5 Hz) | 69.9 | CH | C-3(C*), C-5(C*) | H-5(C*), H$_3$-6(C*) |
| 5C | 3.75 (dq, J = 6.2 and 2.5 Hz) | 72.1 | CH | C-1(C*), C-4(C*), C-6(C*) | H-1(C*), H-3(C*), H-4(C*), |
| 6C | 1.54 (d, J = 6.2 Hz) | 17.5 | CH$_3$ | C-4(C*), C-5(C*) | H-4(C*), H-5(C*) |
| 1D | 5.55 (dd, J = 9.6 and 2.0 Hz) | 98.4 | CH | C-3(C*) | H-2a(D*), H-2e(D*), H-5(D*), H-3(C*) |
| 2aD | 1.89 (dd, J = 13.0 and 9.6 Hz) | 45.5 | CH$_2$ | C-1(D*), C-3(D*), C-4(D*) | H-1(D*), H-4(D*) |
| 2eD | 2.32 (dd, J = 13.0 and 2.0 Hz) | | | | H-1(D*) |
| 3D | — | 71.2 | CH | | H-1(D*) |

TABLE 4-continued $^1$H- and $^{13}$C-NMR data of 3A-deolivosyl-MTM [formula (XI)] (Pyridine-$d_5$, 400 MHz).

| C | $^1$H-NMR δ (J in Hz) | $^{13}$C-NMR (δ) | C | HMBC | NOESY |
|---|---|---|---|---|---|
| 4D | 3.38 (d, J = 9.2 Hz) | 77.7 | CH | C-3(D*), C-5(D*) | H$_3$-3(D*), H$_3$-6(D*), H2a(D*) |
| 5D | 4.29 (dq, J = 9.2 and 6.0 Hz) | 71.9 | CH | C-1(D*), C-4(D*), C-6(D*) | H-1(D*), H$_3$-6(D*) |
| 6D | 1.61 (d, J = 6.0 Hz) | 19.0 | CH$_3$ | C-4(D*), C-5(D*) | H-4(D*), H-5(D*) |
| 3D-Me | 1.50 (s) | 28.2 | CH$_3$ | C-2(D*), C-4(D*), C-3(D*) | H-4(D*) |

*A = B = C = D: sugars

TABLE 5

$^1$H- and $^{13}$C-NMR data of demycarosyl-MTM [formula (XII)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1 | — | 204.4 | C | | |
| 2 | 4.95 d (11.6) | 78.0 | CH | C-1, C-1C, C-3, C-4, C-1' | H-1C, H-3, H-4a, H-4e |
| 3 | 3.48 (m) | 42.6 | C | C-2, C-4, C-1' | H-2, H-4a, H-4e, H-1' |
| 4a | 3.10 dd (5.9 and 3.6) | 28.5 | CH2 | C-2, C-3, C-1' | H-3, H-2 |
| 4e | 3.26 dd (15.9 and 13.0) | | | | H-3, H-2 |
| 4a | — | 137.2 | C | | |
| 5 | 7.04 (s) | 102.1 | CH | C-6, C-8a, C-7, C-10 | H-10, H-1A, H-5A |
| 6 | — | 160.5 | C | | |
| 7 | — | 111.7 | C | | |
| 7-CH3 | 2.47 (s) | 9.1 | CH3 | C-6, C-7, C-8 | |
| 8 | — | 156.9 | C | | |
| 8a | — | 109.3 | C | | |
| 9 | — | 165.7 | C | | |
| 9a | — | 108.8 | C | | |
| 10 | 6.63 (s) | 117.4 | CH | C-5, C-8a, C-9a, C-10a | H-5, H-1A, H-4a, H-4e |
| 10a | — | 139.5 | C | | |
| 1' | 5.47 d (1.2) | 83.0 | CH | C-2, C-3, C-4, 1'-OCH$_3$, C-2' | H-2, H-3, 1'-OCH$_3$ |
| 1'-OCH3 | 3.69 (s) | 59.2 | | C-1', C-2', C-3 | |
| 2' | — | 213.5 | C | | |
| 3' | 4.69 d (2.8) | 81.2 | CH | C-2', C-4', C-5' | H-4', H-5' |
| 4' | 4.84 dq (6.2 and 2.8) | 69.5 | CH | C-2', C-3', C-5' | H-5', H-3' |
| 5' | 1.58 d (6.2) | 20.8 | CH3 | C-3', C-4' | H-4', H-3' |
| 1A | 5.68 dd (9.6 and 2.0) | 97.9 | CH | C-6 | H-2Ae, H-3A, H-5A, H-5, H-10 |
| 2Aa | 2.25 ddd (12, 12 and 9.6) | 37.8 | CH$_2$ | C-1A, C-3A, C-4A | H-2Ae, H-4A, |
| 2Ae | 2.72 ddd (12, 5.0 and 2.0) | | | | H-1A, H-3A, H-2Aa |
| 3A | 4.29 ddd (12, 9.0 and 5.0) | 80.1 | CH2 | C-1B, C-4A | H-1A, H-1B, H-5A, H-2Ae |
| 4A | 3.62 t (9.0) | 75.9 | CH | C-3A, C-5A, C-6A | H-2aA, H$_3$-6A |
| 5A | 4.02 dq (9.0 and 6.0) | 73.7 | CH | C-1A, C-3A, C-4A, C-6A | H-1A, H-3A, H$_3$-6A |
| 6A | 1.70 d (6.0) | 19.2 | CH$_3$ | C-4A, C-5A | H-4A, H-5A |
| 1B | 5.05 dd (9.6 and 2.0) | 99.3 | CH | C-3A, | H-2Be, H-3A, H-3B, H-5B |
| 2Ba | 2.17 ddd (12, 12 and 9.6) | 41.4 | CH$_2$ | C-1B, C-3B, C-4B | H-2Be, H-4B, |
| 2Be | 2.64 ddd (12, 5.0 and 2.0) | | | | H-1B, H-3B, H-2Ba |
| 3B | 4.14 ddd (12, 9.0 and 5.0) | 72.2 | CH | C-4B | H-1B, H-2Be, H-5B |
| 4B | 3.58 t (9.0) | 78.5 | CH | C-3B, C-5B, C-6B | H-2Ba, H$_3$-6B |
| 5B | 3.75 dq (9.0 and 6.0) | 72.5 | CH | C-1B, C-3B, C-4B, C-6B | H-1B, H-3B, H$_3$-6B |
| 6B | 1.64 d (6.0) | 19.1 | CH$_3$ | C-4B, C-5B | H-4B, H-5B |
| 1C | 5.39 dd (J = 9.6 and 2.0z) | 101.8 | CH | C-2 | H-2, H-3C, H-5C, H-2Ce |
| 2Ca | 2.00 ddd (12, 12 and 9.6) | 38.5 | CH$_2$ | C-1C, C-3C, C-4C | H-2Ce, H-4C, |
| 2Ce | 2.96 ddd (12, 5.0 and 2.0) | | | | H-1C, H-3C, H-2Ca |
| 3C | 4.06 ddd (12, 9.0 and 5.0) | 81.5 | CH | C-1D, C-4C | H-1C, H-1D, H-5C, H-2Ce |
| 4C | 3.47 t (9.0) | 76.3 | CH | C-3C, C-5C, C-6C | H-2aC, H$_3$-6C |
| 5C | 3.68 dq (9.0 and 6.0) | 73.4 | CH | C-1C, C-4C, C-6C | H-3C, H-1C, H$_3$-6C |
| 6C | 1.61 d (6.0) | 18.9 | CH$_3$ | C-4C, C-5C | H-4C, H-5C |
| 1D | 4.79 dd (9.6 and 2.0) | 100.6 | CH | C-3C | H-3C, H-3D, H-5D, H-2e-D |
| 2Da | 2.44 ddd (12, 12 and 9.6) | 36.4 | CH$_2$ | C-1D, C-3D, C-4D | H-2De, H-4D, |
| 2De | 2.30 ddd (12, 5.0 and 2.0) | | | | H-1D, H-3D, H-2Da |
| 3D | 4.18 ddd (12, 5.0 and 2.5) | 70.0 | CH | C-2D, C-4D | H-1D, H-2De, H-5D |
| 4D | 3.92 brd (2.5) | 71.2 | CH | C-3D, C-5D | H$_3$-6D |
| 5D | 3.73 dq (6.0 and 2.5) | 73.8 | CH | C-4D, C-6D | H-1D, H-3D, H$_3$-6D |
| 6D | 1.57 d (6.0) | 17.7 | CH$_3$ | C-4D, C-5D | H-4D, H-5D |

*A = B = C = D: sugars

TABLE 6

$^1$H- and $^{13}$C-NMR data of 6-dediolivosyl-6-β-D-amicetosyl-MTM [formula (XIII)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1 | — | 204.4 | C | | |
| 2 | 4.95 d (11.6) | 78.0 | CH | C-1, C-1C, C-3, C-4, C-1' | H-1C, H-3, H-4a, H-4e |
| 3 | 3.48 (m) | 42.5 | C | C-2, C-4, C-1' | H-2, H-4a, H-4e, H-1' |
| 4a | 3.12 dd (15.9 and 3.6) | 28.3 | CH$_2$ | C-2, C-3, C-1' | H-3, H-2 |
| 4e | 3.30 dd (15.9 and 13.0) | | | | H-3, H-2 |
| 4a | — | 137.1 | C | | |
| 5 | 7.05 (s) | 102.2 | CH | C-6, C-8a, C-7, C-10 | H-10, H-1A, H-5A |
| 6 | — | 160.6 | C | | |
| 7 | — | 111.7 | C | | |
| 7-CH$_3$ | 2.45 (s) | 9.1 | CH$_3$ | C-6, C-7, C-8 | |
| 8 | — | 156.9 | C | | |
| 8a | — | 109.3 | C | | |
| 9 | — | 165.8 | C | | |
| 9a | — | 108.7 | C | | |
| 10 | 6.65 (s) | 117.4 | CH | C-5, C-8a, C-9a, C-10a | H-5, H-1A, H-4a, H-4e |
| 10a | — | 139.5 | C | | |
| 1' | 5.49 d (1.2) | 83.0 | CH | C-2, C-3, C-4, 1'-OCH$_3$, C-2' | H-2, H-3, 1'-OCH$_3$ |
| 1'-OCH$_3$ | 3.69 (s) | 59.1 | CH$_3$ | C-1', C-2', C-3 | |
| 2' | — | 213.7 | C | | |
| 3' | 4.70 d (2.8) | 81.3 | CH | C-2', C-4', C-5' | H-4', H-5' |
| 4' | 4.85 dq (6.2 and 2.8) | 69.5 | CH | C-2', C-3', C-5' | H-5', H-3' |
| 5' | 1.59 d (6.2) | 20.9 | CH$_3$ | C-3', C-4' | H-4', H-3' |
| 1A | 5.60 dd (8.64 and 2.5) | 98.4 | CH | C-6 | H-2Aa, H-3Aa, H-5, H-5A, |
| 2Aa | 2.12 (m) | 32.0 | CH$_2$ | C-1A, C-3A, C-4A | H-1A, H-4A, H-2Ae |
| 2Ae | | | | | H-1A, H-2Aa, H-3Aa |
| 3Aa | 1.97 (m) | 31.4 | CH$_2$ | C-2A, C-4A | H-1A, H-5A, H-3Ae |
| 3Ae | 2.35 (m) | | | | H-3Aa, H$_3$-6A |
| 4A | 3.67 (m) | 71.3 | CH | C-3A, C-5A, C-6A | H-2aa, H$_3$-6A |
| 5A | 4.00 dq (8.5 and 6.0) | 77.8 | CH | C-1A, C-3A, C-4A, C-6A | H-1A, H-3Aa, H$_3$-6A |
| 6A | 1.67 d (6.0) | 19.4 | CH$_3$ | C-4A, C-5A | H-4A, H-5A |
| 1C | 5.39 dd (9.6 and 2.0) | 101.8 | CH | C-2 | H-2, H-2Ce, H-3C, H-5C |
| 2Ca | 2.02 ddd (12, 12 and 9.6) | 38.5 | CH$_2$ | C-1C, C-3C, C-4C | H-4C |
| 2Ce | 2.99 ddd (12, 5.0 and 2.0) | | | | H-1C |
| 3C | 4.05 ddd (12, 9.0 and 5.0) | 81.5 | CH | C-1D, C-4C | H-1C, H-1D, H-5C, H-2Ce |
| 4C | 3.46 t (9.0) | 76.2 | CH | C-3C, C-5C, C-6C | H-2Ca, H$_3$-6C |
| 5C | 3.68 dq (9.0 and 6.0) | 73.3 | CH | C-1C, C-4C, C-6C | H-1C, H-3C, H$_3$-6C |
| 6C | 1.61 d (6.0) | 19.5 | CH$_3$ | C-4C, C-5C | H-4C, H-5C |
| 1D | 4.79 dd (9.6 and 2.0) | 100.3 | CH | C-3C | H-3C, H-3D, H-2De, H-5D |
| 2Da | 2.42 ddd (12, 12 and 9.6) | 33.1 | CH$_2$ | C-1D, C-3D, C-4D | H-1D |
| 2De | 2.22 ddd (12, 5.0 and 2.0) | | | | H-1D |
| 3D | 4.22 ddd (12, 5.0 and 2.5) | 77.0 | CH | C-1E, C-4D | H-1E, H-1D, H-2De, H-5D |
| 4D | 4.10 br.d (2.5) | 70.0 | CH | C-3D, C-5D | H$_3$-6D |
| 5D | 3.75 dq (6.0 and 2.5) | 72.2 | CH | C-1D, C-4D, C-6D | H-1D, H-3D, H$_3$-6D |
| 6D | 1.54 d (6.0) | 17.6 | CH$_3$ | C-4D, C-5D | H-5D |
| 1E | 5.55 dd (9.6 and 2.0) | 99.6 | CH | C-3D | H-5E, H-3D, H-2Ea, H-2Ee |
| 2Ea | 1.86 dd (13.1 and 9.6) | 45.6 | CH$_2$ | C-1E, C-3E, C-4E | H-4E, H-2ee |
| 2Ee | 2.33 dd (13.1 and 2.0) | | | | H-1E, H-2Ea |
| 3E | — | 71.3 | C | | — |
| 3E-CH$_3$ | 1.58 (s) | 28.2 | CH$_3$ | C-2E, C-4E, C-3E | H-4E |
| 4E | 3.37 d (9.2) | 77.8 | CH | C-3E, C-5E | H-2aE, H$_3$-3E, H$_3$-6E |
| 5E | 4.28 dq (9.2 and 6.0) | 72.9 | CH | C-1E, C-4E, C-6E | H-1E, H$_3$-6E |
| 6E | 1.61 d (6.0) | 19.1 | CH$_3$ | C-4E, C-5E | H-5E |

*A = B = C = D = E: sugars

TABLE 7

$^1$H- and $^{13}$C-NMR data of deoliosyl-demycarosyl-3C-β-D-boivinosyl-MTM [formula (XVII)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1 | — | 204.5 | C | | |
| 2 | 4.94 d (11.6) | 77.6 | CH | C-1, C-1C, C-3, C-4, C-1' | H-1C, H-3, H-4a, H-4e |
| 3 | 3.48 (m) | 42.6 | C | C-2, C-4, C-1' | H-2, H-4a, H-4e, H-1' |
| 4a | 3.10 dd (15.9 and 3.6) | 28.1 | CH2 | C-2, C-3, C-1' | H-3, H-2 |
| 4e | 3.26 dd (15.9 and 13.0) | | | | H-3, H-2 |
| 4a | — | 137.2 | C | | |
| 5 | 7.04 (s) | 102.2 | CH | C-6, C-8a, C-7, C-10 | H-10, H-1A, H-5A |
| 6 | — | 160.4 | C | | |

TABLE 7-continued $^1$H- and $^{13}$C-NMR data of deoliosyl-demycarosyl-3C-β-D-boivinosyl-MTM [formula (XVII)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 7 | — | 111.9 | C | | |
| 7-CH$_3$ | 2.47 (s) | 9.1 | CH3 | C-6, C-7, C-8 | |
| 8 | — | 157.0 | C | | |
| 8a | — | 109.4 | C | | |
| 9 | — | 165.8 | C | | |
| 9a | — | 108.9 | C | | |
| 10 | 6.62 (s) | 117.0 | CH | C-5, C-8a, C-9a, C-10a | H-5, H-1A, H-4a, H-4e |
| 10a | — | 139.5 | C | | |
| 1' | 5.46 d (1.2) | 83.0 | CH | C-2, C-3, C-4, 1'-OCH$_3$, C-2' | H-2, H-3, 1'-OCH$_3$ |
| 1'-OCH$_3$ | 3.69 (s) | 59.2 | | C-1', C-2', C-3 | |
| 2' | — | 213.5 | C | | |
| 3' | 4.69 d (2.8) | 81.2 | CH | C-2', C-4', C-5' | H-4', H-5' |
| 4' | 4.84 dq (6.0 and 2.8) | 69.5 | CH | C-2', C-3', C-5' | H-5', H-3' |
| 5' | 1.59 d (6.0) | 20.8 | CH3 | C-3', C-4' | H-4', H-3' |
| 1A | 5.67 dd (9.6 and 2.0) | 97.9 | CH | C-6 | H-3A, H-5A, H-2Aa, H-2Ae, H-5, H-10 |
| 2Aa | 2.23 ddd (12.0, 12.0 and 9.6) | 37.8 | CH$_2$ | C-1A, C-3A, C-4A | H-1A, H-4A, H-2Ae |
| 2Ae | 2.70 ddd (12.0, 5.0 and 2.0) | | | | H-1A, H-3A, H-2Aa |
| 3A | 4.27 ddd (12, 9.2 and 5.0) | 74.2 | CH2 | C-1B, C-4A | H-1A H-1B, H-5A, H-2Ae |
| 4A | 3.61 t (9.2) | 80.1 | CH | C-3A, C-5A, C-6A | H-2Aa, H$_3$-6A |
| 5A | 4.01 dq (9.2 and 6.0) | 73.8 | CH | C-1A, C-3A, C-4A, C-6A | H-1A, H-3A, H$_3$-6A |
| 6A | 1.71 d (J = 6.0) | 19.2 | CH$_3$ | C-4A, C-5A | H-4A, H-5A |
| 1B | 5.05 dd (9.6 and 2.0) | 99.4 | CH | C-3A | H-2Ba, H-2Be, H-3A, H-3B, H-5B |
| 2Ba | 2.14 ddd (12, 12 and 9.6) | 41.4 | CH$_2$ | C-1B, C-3B, C-4B | H-1B, H-4B |
| 2Be | 2.64 ddd (12, 5.0 and 2.0) | | | | H-1B |
| 3B | 4.14 ddd (12, 9.0 and 5.0) | 72.2 | CH | C-4B | H-2Be, H-1B, H-5B |
| 4B | 3.57 t (9.0) | 78.5 | CH | C-3B, C-5B, C-6B | H-2Ba, H$_3$-6B |
| 5B | 3.73 dq (9.0 and 6.0) | 73.4 | CH | C-1B, C-3B, C-4B, C-6B | H-1B, H-3B, H$_3$-6B |
| 6B | 1.63 d (6.0) | 19.1 | CH$_3$ | C-4B, C-5B | H-5B |
| 1C | 5.38 dd (9.6 and 2.0) | 101.8 | CH | C-2 | H-2, H-3C, H-5C, H-2Ce |
| 2Ca | 2.00 ddd (12, 12 and 9.6) | 38.2 | CH$_2$ | C-1C, C-3C, C-4C | H-4C |
| 2Ce | 2.92 ddd (12, 5.0 and 2.0) | | | | H-1C |
| 3C | 4.05 ddd (12, 9.0 and 5.0) | 81.5 | CH | C-1D, C-4C | H-1C, H-1D, H-5C, H-2Ce |
| 4C | 3.47 t (9.0) | 76.0 | CH | C-3C, C-5C, C-6C | H-2Ca, H$_3$-6C |
| 5C | 3.67 dq (9.0 and 6.0) | 73.6 | CH | C-4C, C-6C | H-3C, H-1C, H$_3$-6C |
| 6C | 1.60 d (6.0) | 18.9 | CH$_3$ | C-4C, C-5C | H-5C, H-4C |
| 1D | 5.54 dd (10.0 and 3.0) | 99.4 | CH | C-3C | H-3D, H-5D, H-2De, H-3C |
| 2Da | 2.55 ddd (13, 10 and 3.0) | 41.4 | CH$_2$ | C-1D, C-3D, C-4D | H-1D, H-2De |
| 2De | 2.28 ddd (13, 3.0 and 3.0) | | | | |
| 3D | 3.77 ddd (3.2, 3.0 and 1.2) | 71.4 | CH | C-4D | H-2Da, H-4D, H$_3$-6D, H-5D |
| 4D | 3.87 dd (3.2 and 1.2) | 71.0 | CH | C-3D, C-5D | H-3D, H-5D, H$_3$-6D |
| 5D | 4.64 dq (6.0 and 3.2) | 70.3 | CH | C-1D, C-4D, C-6D | H-1D, H-3D, H$_3$-6D |
| 6D | 1.57 d (6.0) | 17.6 | CH$_3$ | C-4D, C-5D | H-4D, H-5D, H-3D |

*= B = C = D: sugars

TABLE 8

$^1$H- and $^{13}$C-NMR data of 6-dediolivosyl-6-β-D-amicetosyl-deoliosyl-demycarosyl-3C-β-D-boivinosyl-MTM [formula (XVIII)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1 | — | 204.3 | C | | |
| 2 | 4.38 d (11.6) | 78.1 | CH | C-1, C-1C, C-3, C-4, C-1' | H-1C, H-3, H-4a, H-4e |
| 3 | 3.46 (m) | 42.6 | C | C-2, C-4, C-1' | H-2, H-4a, H-4e, H-1' |
| 4a | 3.11 dd (15.9 and 3.6) | 26.8 | CH2 | C-2, C-3, C-1' | H-3, H-2 |
| 4e | 3.27 dd (15.9 and 13.0) | | | | H-3, H-2 |
| 4a | — | 137.1 | C | | |
| 5 | 7.04 (s) | 102.3 | CH | C-6, C-8a, C-7, C-10 | H-10, H-1A, H-5A |
| 6 | — | 160.6 | C | | |
| 7 | — | 111.7 | C | | |
| 7-CH3 | 2.45 (s) | 9.19 | CH3 | C-6, C-7, C-8 | |

TABLE 8-continued

¹H- and ¹³C-NMR data of 6-dediolivosyl-6-β-D-amicetosyl-deoliosyl-demycarosyl-3C-β-D-boivinosyl-MTM [formula (XVIII)] (Pyridine-d5, 400 MHz).

| Position | ¹H-NMR, 400 MHz; δ in ppm, multiplicity (J in Hz) | ¹³C-NMR, 100.6 MHz; δ in ppm | Multiplicity | HMBC | NOESY |
|---|---|---|---|---|---|
| 8 | — | 156.9 | C | | |
| 8a | — | 109.3 | C | | |
| 9 | — | 165.8 | C | | |
| 9a | — | 108.7 | C | | |
| 10 | 6.64 (s) | 117.9 | CH | C-5, C-8a, C-9a, C-10a | H-5, H-1A, H-4a, H-4e |
| 10a | — | 139.5 | C | | |
| 1' | 5.48 d (1.2) | 83.1 | CH | C-2, C-3, C-4, 1'-OCH₃, C-2' | H-2, H-3, 1'-OCH₃ |
| 1'-OCH3 | 3.70 (s) | 59.2 | | C-1', C-2', C-3 | |
| 2' | — | 213.6 | C | | |
| 3' | 4.70 d (2.8) | 81.3 | CH | C-2', C-4', C-5' | H-4', H-5' |
| 4' | 4.84 dq (6.2 and 2.8) | 69.5 | CH | C-2', C-3', C-5' | H-5', H-3' |
| 5' | 1.60 (d, J = 6.2) | 20.8 | CH3 | C-3', C-4' | H-4', H-3' |
| 1A | 5.59 (dd, J = 9.6 and 2.0) | 99.6 | CH | C-6 | H-2Aa, H-3Aa, H-5, H-5A, |
| 2Aa | 2.15 (m) | 31.4 | CH₂ | C-1A, C-3A, C-4A | H-1A, H-4A, H-2Ae |
| 2Ae | 2.41 (m) | | | | H-1A, H-2Aa, H-3Aa |
| 3Aa | 1.97 (m) | 32.1 | CH2 | C-2A, C-4A | H-1A, H-5A, H-3Ae |
| 3Ae | 2.38 (m) | | | | H-3Aa, H₃-6A |
| 4ᵃ | 3.68 (m) | 71.3 | CH | C-3A, C-5A, C-6A | H-2Aa, H₃-6A |
| 5ᵃ | 4.01 dq (9.0 and 6.0) | 77.89 | CH | C-1A, C-3Aa, C-4A, C-6A | H-1A, H-3Aa, H₃-6A |
| 6A | 1.67 d (6.0) | 19.4 | CH₃ | C-4A, C-5A | H-4A, H-5A |
| 1C | 5.38 dd (9.6 and 2.0) | 101.8 | CH | C-2 | H-2, H-2Ce, H-3C, H-5C |
| 2Ca | 2.00 ddd (12, 12 and 9.6) | 38.6 | CH₂ | C-1C, C-3C, C-4C | H-4C |
| 2Ce | 2.93 ddd (12, 5.0 and 2.0) | | | | H-1C |
| 3C | 4.02 ddd (12, 9.0 and 5.0) | 81.4 | CH | C-1D, C-4C | H-1C, H-1D, H-4C, H-5C, H-2Ce |
| 4C | 3.45 t (9.0) | 76.3 | CH | C-3C, C-5C, C-6C | H-2Ca, H₃-6C |
| 5C | 3.67 dq (9.0 and 6.0) | 73.4 | CH | C-1C, C-4C, C-6C | H-1C, H-3C, H₃-6C |
| 6C | 1.61 d (6.0) | 19.1 | CH₃ | C-4C, C-5C | H-4C, H-5C |
| 1D | 4.72 dd (10 and 2.0) | 102.0 | CH | C-3C | H-3C, H-2De, H-5D |
| 2Da | 2.26 ddd (13, 10 and 3.0) | 31.45 | CH₂ | C-1D, C-3D, C-4D | H-1D, H-2De |
| 2De | 1.71 ddd (13, 3.0 and 2.0) | | | | |
| 3D | 3.71 ddd (3.0, 3.0 and 1.2) | 66.2 | CH | C-4D | H-2Da, H-4D, H₃-6D, H-5D |
| 4D | 3.65 dd (2.5, and 1.2) | 71.3 | CH | C-3D, C-5D | H-3D, H-5D, H₃-6D |
| 5D | 3.78 dq (6.0 and 2.5) | 75.58 | CH | C-1D, C-4D, C-6D | H-1D, H-3D, H₃-6D |
| 6D | 1.48 d (6.0) | 18.14 | CH₃ | C-4D, C-5D | H-4D, H-5D, H-3D |

*A = B = C = D: sugars

TABLE 9

¹H- and ¹³C-NMR data of deoliosyl-demycarosyl-3C-β-D-olivosyl-3D-β-D-digitoxosyl-MTM [formula (XIX)] (Pyridine-d5, 400 MHz).

| Position | ¹H-NMR, 400 MHz; δ in ppm, multiplicity (J in Hz) | ¹³C-NMR, 100.6 MHz; δ in ppm | Multiplicity | HMBC | NOESY |
|---|---|---|---|---|---|
| 1 | — | 204.4 | C | | |
| 2 | 4.96 d (11.6) | 77.9 | CH | C-1, C-1C, C-3, C-4, C-1' | H-1C, H-3, H-4a, H-4e |
| 3 | 3.48 (m) | 42.6 | C | C-2, C-4, C-1' | H-2, H-4a, H-4e, H-1' |
| 4a | 3.10 dd (15.9 and 3.6) | 28.1 | CH2 | C-2, C-3, C-1' | H-3, H-2 |
| 4e | 3.27 dd (15.9 and 13.0) | | | | H-3, H-2 |
| 4a | — | 137.1 | C | | |
| 5 | 7.05 (s) | 102.2 | CH | C-6, C-8a, C-7, C-10 | H-10, H-1A, H-5A |
| 6 | — | 160.5 | C | | |
| 7 | — | 111.7 | C | | |
| 7-CH₃ | 2.47 (s) | 8.9 | CH3 | C-6, C-7, C-8 | |
| 8 | — | 157.0 | C | | |
| 8a | — | 109.3 | C | | |
| 9 | — | 165.8 | C | | |
| 9a | — | 108.8 | C | | |
| 10 | 6.63 (s) | 117.4 | CH | C-5, C-8a, C-9a, C-10a | H-5, H-1A, H-4a, H-4e |
| 10a | — | 139.5 | C | | |
| 1' | 5.49 d (1.2) | 82.9 | CH | C-2, C-3, C-4, 1'-OCH₃, C-2' | H-2, H-3, 1'-OCH₃ |
| 1'-OCH3 | 3.71 (s) | 59.5 | | C-1', C-2', C-3 | |
| 2' | — | 213.4 | C | | |
| 3' | 4.70 d (2.8) | 81.1 | CH | C-2', C-4', C-5' | H-4', H-5' |
| 4' | 4.84 dq (6.2 and 2.8) | 69.3 | CH | C-2', C-3', C-5' | H-5', H-3' |
| 5' | 1.59 d (6.2) | 20.6 | CH3 | C-3', C-4' | H-4', H-3' |

TABLE 9-continued

¹H- and ¹³C-NMR data of deoliosyl-demycarosyl-3C-β-D-olivosyl-3D-β-D-digitoxosyl-MTM [formula (XIX)] (Pyridine-d5, 400 MHz).

| Position | ¹H-NMR, 400 MHz; δ in ppm, multiplicity (J in Hz) | ¹³C-NMR, 100.6 MHz; δ in ppm | Multiplicity | HMBC | NOESY |
|---|---|---|---|---|---|
| 1A | 5.67 dd (9.6 and 2.0) | 97.9 | CH | C-6 | H-3A, H-5A, H-2Aa, H-2Ae, H-5, H-10 |
| 2Aa | 2.25 ddd (12, 12 and 9.6) | 37.7 | CH$_2$ | C-1A, C-3A, C-4A | H-1A, H-4A, H-2Ae |
| 2Ae | 2.71 ddd (12, 5.0 and 2.0) | | | | H-1A, H-3A, H-2Aa |
| 3A | 4.28 ddd (12, 9.0 and 5.0) | 80.5 | CH2 | C-1B, C-4A | H-1A, H-1B, H-5A, H-2Ae |
| 4A | 3.62 t (9.0) | 75.8 | CH | C-3A, C-5A, C-6A | H-2Aa, H$_3$-6A |
| 5A | 4.01 dq (9.0 and 6.0) | 73.6 | CH | C-1A, C-3A, C-4A, C-6A | H-1A, H-3A, H$_3$-6A |
| 6A | 1.70 d (6.0) | 19.0 | CH$_3$ | C-4A, C-5A | H-4A, H-5A |
| 1B | 5.05 dd (9.6 and 2.0) | 99.4 | CH | C-3A | H-2Ba, H-2Be, H-3A, H-3B, H-5B |
| 2Ba | 2.14 ddd (12, 12 and 9.6) | 41.2 | CH$_2$ | C-1B, C-3B, C-4B | H-1B, H-4B |
| 2Be | 2.65 ddd (12, 5.0 and 2.0) | | | | H-1B |
| 3B | 4.16 ddd (12, 9.0 and 5.0) | 72.2 | CH | C-4B | H-2Be, H-1B, H-5B |
| 4B | 3.57 t (9.0) | 77.6 | CH | C-3B, C-5B, C-6B | H-2Ba, H$_3$-6B |
| 5B | 3.74 dq (9.0 and 6.0) | 73.7 | CH | C-1B, C-3B, C-4B, C-6B | H-1B, H-3B, H$_3$-6B |
| 6B | 1.64 d (6.0) | 18.3 | CH$_3$ | C-4B, C-5B | H-5B |
| 1C | 5.39 dd (9.6 and 2.0) | 101.6 | CH | C-2 | H-2, H-3C, H-5C, H-2Ce |
| 2Ca | 2.00 ddd (12, 12 and 9.6) | 38.4 | CH$_2$ | C-1C, C-3C, C-4C | H-4C |
| 2Ce | 3.00 ddd (12, 5.0 and 2.0) | | | | H-1C |
| 3C | 4.10 ddd (12, 9.0 and 5.0) | 81.0 | CH | C-1D, C-4C | H-1C, H-1D, H-5C, H-2Ce |
| 4C | 3.50 t (9.0) | 76.1 | CH | C-3C, C-5C, C-6C | H-2Ca, H$_3$-6C |
| 5C | 3.69 dq (9.0 and 6.0) | 73.6 | CH | C-4C, C-6C | H-3C, H-1C, H$_3$-6C |
| 6C | 1.60 d (6.0) | 18.9 | CH$_3$ | C-4C, C-5C | H-5C, H-4C |
| 1D | 4.90 dd (9.6 and 2.0) | 99.4 | CH | C-3C | H-3D, H-5D, H-2De, H-3C |
| 2Da | 1.90 ddd (12, 12 and 9.6) | 32.3 | CH$_2$ | C-1D, C-3D, C-4D | |
| 2De | 2.18 ddd (12, 5.0 and 2.0) | | | | H-1D |
| 3D | 4.04 ddd (12, 9.0 and 5.0) | 80.1 | CH | C-1E, C-4D | H-1D, H-2De, H-5D, H-1E |
| 4D | 3.44 T (9.0) | 75.8 | CH | C-3D, C-5D | H-2Da, H$_3$-6D |
| 5D | 3.66 dq (9.0 and 6.0) | 73.3 | CH | C-4D, C-6D | H-1D, H-3D, H$_3$-6D |
| 6D | 1.58 d (6.0) | 18.7 | CH$_3$ | C-4D, C-5D | H-4D, H-5D |
| 1E | 4.88 dd (10 and 2.0) | 101.3 | CH | C-3D | H-5E, H-2Ea, H-2Ee, H-3D |
| 2Ea | 1.75 ddd (13, 10.0 and 2.5) | 31.1 | CH$_2$ | C-1E, C-3E, C-4E | |
| 2Ee | 2.21 ddd (13, 2.5 and 2.0) | | | | H-1E, H-2Ea |
| 3E | 3.52 ddd (2.8, 2.5, and 2.5) | 71.3 | CH | C-4E | H-4E |
| 4E | 3.49 dd (9.0 and 2.8) | 77.6 | CH | C-3E, C-5E | H-2Ea, H-3E, H$_3$-6E |
| 5E | 3.66 dq (9.0 and 6.0) | 73.3 | CH | C-1E, C-4E, C-6E | H$_3$-6E, H-1E |
| 6E | 1.55 d (6.0) | 18.6 | CH$_3$ | C-4E, C-5E | H-5E |

*A = B = C = D = E: sugars

TABLE 10

¹H- and ¹³C-NMR data of 6-dediolivosyl-6-β-D-amicetosyl-deoliosyl-demycarosyl-3C-β-D-olivosyl-3D-β-D-digitoxosyl-MTM [(formula XX)] (Pyridine-d5, 400 MHz).

| Position | ¹H-NMR, 400 MHz; δ in ppm, multiplicity (J in Hz) | ¹³C-NMR, 100.6 MHz; δ in ppm | Multiplicity | HMBC | NOESY |
|---|---|---|---|---|---|
| 1 | — | 204.3 | C | | |
| 2 | 4.95 d (11.6) | 78.0 | CH | C-1, C-1C, C-3, C-4, C-1' | H-1C, H-3, H-4a, H-4e |
| 3 | 3.48 (m) | 42.6 | C | C-2, C-4, C-1' | H-2, H-4a, H-4e, H-1' |
| 4a | 3.10 dd (15.9 and 3.6) | 28.3 | CH$_2$ | C-2, C-3, C-1' | H-3, H-2 |
| 4e | 3.27 dd (15.9 and 13.0) | | | | H-3, H-2 |
| 4a | — | 137.1 | C | | |
| 5 | 7.05 (s) | 102.2 | CH | C-6, C-8a, C-7, C-10 | H-10, H-1A, H-5A |
| 6 | — | 160.6 | C | | |
| 7 | — | 111.7 | C | | |
| 7-CH3 | 2.45 (s) | 9.1 | CH$_3$ | C-6, C-7, C-8 | |
| 8 | — | 156.9 | C | | |
| 8a | — | 109.3 | C | | |
| 9 | — | 165.9 | C | | |
| 9a | — | 108.7 | C | | |
| 10 | 6.66 (s) | 117.4 | CH | C-5, C-8a, C-9a, C-10a | H-5, H-1A, H-4a, H-4e |
| 10a | — | 139.5 | C | | |
| 1' | 5.49 d (1.2) | 83.1 | CH | C-2, C-3, C-4, 1'-OCH$_3$, C-2' | H-2, H-3, 1'-OCH$_3$ |

TABLE 10-continued $^1$H- and $^{13}$C-NMR data of 6-dediolivosyl-6-β-D-amicetosyl-deoliosyl-demycarosyl-3C-β-D-olivosyl-3D-β-D-digitoxosyl-MTM [(formula XX)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1'-OCH3 | 3.71 (s) | 59.2 | CH$_3$ | C-1', C-2', C-3 | |
| 2' | — | 213.6 | C | | |
| 3' | 4.71 d (2.8) | 81.3 | CH | C-2', C-4', C-5' | H-4', H-5' |
| 4' | 4.84 dq (6.2 and 2.8) | 69.5 | CH | C-2', C-3', C-5' | H-5', H-3' |
| 5' | 1.59 d (6.2) | 20.8 | CH$_3$ | C-3', C-4' | H-4', H-3' |
| 1A | 5.59 dd (8.64 and 2.5) | 99.7 | CH | C-6 | H-2Aa, H-3Aa, H-5, H-5A, |
| 2Aa | 2.17 (m) | 31.4 | CH$_2$ | C-1A, C-3A, C-4A | H-1A, H-4A, H-2Ae |
| 2Ae | 2.43 (m) | | | | H-1A, H-2Aa, H-3Aa |
| 3Aa | 1.96 (m) | 32.1 | CH$_2$ | C-2A, C-4A | H-1A, H-5A, H-3Ae |
| 3Ae | 2.40 (m) | | | | H-3Aa, H$_3$-6A |
| 4A | 3.69 (m) | 71.3 | CH | C-3A, C-5A, C-6A | H-2Aa, H$_3$-6A |
| 5A | 4.02 dq (8.5 and 6.0) | 77.7 | CH | C-1A, C-3A, C-4A, C-6A | H-1A, H-3Aa, H$_3$-6A |
| 6A | 1.67 d (6.0) | 19.4 | CH$_3$ | C-4A, C-5A | H-4A, H-5A |
| 1C | 5.39 d (9.6 and 2.0) | 101.7 | CH | C-2 | H-2, H-3C, H-5C, H-2Ce |
| 2Ca | 2.00 ddd (12, 12 and 9.6) | 38.4 | CH$_2$ | C-1C, C-3C, C-4C | H-4C |
| 2Ce | 2.99 ddd (12, 5.0 and 2.0) | | | | H-1C |
| 3C | 4.10 ddd (12, 9.0 and 5.0) | 81.1 | CH | C-1D, C-4C | H-1C, H-1D, H-5C, H-2Ce |
| 4C | 3.49 t (9.0) | 76.2 | CH | C-3C, C-5C, C-6C | H-2Ca, H$_3$-6C |
| 5C | 3.68 dq (9.0 and 6.0) | 73.4 | CH | C-4C, C-6C | H-3C, H-1C, H$_3$-6C |
| 6C | 1.61 d (6.0) | 19.1 | CH$_3$ | C-4C, C-5C | H-5C, H-4C |
| 1D | 4.90 dd (9.6 and 2.0) | 99.3 | CH | C-3C | H-3D, H-5D, H-2De, H-3C |
| 2Da | 1.90 ddd (12, 12 and 9.6) | 32.5 | CH$_2$ | C-1D, C-3D, C-4D | |
| 2De | 2.50 ddd (12, 5.0 and 2.0) | | | | H-1D |
| 3D | 4.03 ddd (12, 9.0 and 5.0) | 80.5 | CH | C-1E, C-4D | H-1D, H-2De, H-5D, H-1E |
| 4D | 3.47 t (9.0) | 75.9 | CH | C-3D, C-5D | H-2Da, H$_3$-6D |
| 5D | 3.68 dq (9.0 and 6.0) | 73.3 | CH | C-4D, C-6D | H-1D, H-3D, H$_3$-6D |
| 6D | 1.55 d (6.0) | 18.8 | CH$_3$ | C-4D, C-5D | H-4D, H-5D |
| 1E | 4.88 dd (9.6 and 2.0) | 101.35 | CH | C-3D | H-5E, H-2Ea, H-2Ee, H-3D |
| 2Ea | 1.77 ddd (13, 10 and 2.5) | 31.1 | CH$_2$ | C-1E, C-3E, C-4E | |
| 2Ee | 2.20 ddd (13, 2.5 and 2.0) | | | | H-1E, H-2Ea |
| 3E | 3.52 ddd (2.8, 2.5 and 2.5) | 71.3 | CH | C-4E | H-4E |
| 4E | 3.45 dd (9.0, 2.8) | 71.9 | CH | C-3E, C-5E | H-2Ea, H-3E, H$_3$-6E |
| 5E | 3.68 dq (6.0 and 9.0) | 73.4 | CH | C-1E, C-4E, C-6E | H$_3$-6E, H-1E |
| 6E | 1.58 d (6.0) | 19.1 | CH$_3$ | C-4E, C-5E | H-5E |

*A = B = C = D = E: sugars

TABLE 11

$^1$H- and $^{13}$C-NMR data of 6-dediolivosyl-6-β-D-amicetosyl-deoliosyl-3C-β-D-olivosyl-MTM [formula (XXI)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1 | — | 204.3 | C | | |
| 2 | 4.95 d (11.6) | 78.0 | CH | C-1, C-1C, C-3, C-4, C-1' | H-1C, H-3, H-4a, H-4e |
| 3 | 3.47 (m) | 42.6 | C | C-2, C-4, C-1' | H-2, H-4a, H-4e, H-1' |
| 4a | 3.11 dd (15.9 and 3.6) | 28.1 | CH$_2$ | C-2, C-3, C-1' | H-3, H-2 |
| 4e | 3.27 dd (15.9 and 13.0) | | | | H-3, H-2 |
| 4a | — | 136.4 | C | | |
| 5 | 7.05 (s) | 102.2 | CH | C-6, C-8a, C-7, C-10 | H-10, H-1A, H-5A |
| 6 | — | 160.6 | C | | |
| 7 | — | 111.7 | C | | |
| 7-CH$_3$ | 2.45 (s) | 9.1 | CH$_3$ | C-6, C-7, C-8 | |
| 8 | — | 156.9 | C | | |
| 8a | — | 109.3 | C | | |
| 9 | — | 165.9 | C | | |
| 9a | — | 108.7 | C | | |
| 10 | 6.65 (s) | 117.4 | CH | C-5, C-8a, C-9a, C-10a | H-5, H-1A, H-4a, H-4e |
| 10a | — | 139.5 | C | | |
| 1' | 5.50 d (1.2) | 83.3 | CH | C-2, C-3, C-4, 1'-OCH$_3$, C-2' | H-2, H-3, 1'-OCH$_3$ |
| 1'-OCH$_3$ | 3.71 (s) | 59.2 | CH$_3$ | C-1', C-2', C-3 | |
| 2' | — | 213.6 | C | | |
| 3' | 4.71 d (2.8) | 81.3 | CH | C-2', C-4', C-5' | H-4', H-5' |
| 4' | 4.84 dq (6.2 and 2.8) | 69.5 | CH | C-2', C-3', C-5' | H-5', H-3' |
| 5' | 1.58 d (6.2) | 20.8 | CH$_3$ | C-3', C-4' | H-4', H-3' |

TABLE 11-continued $^1$H- and $^{13}$C-NMR data of 6-dediolivosyl-6-β-D-amicetosyl-deoliosyl-3C-β-D-olivosyl-MTM [formula (XXI)] (Pyridine-d5, 400 MHz).

| Position | $^1$H-NMR, 400 MHz; δ in ppm, multiplicity (J in Hz) | $^{13}$C-NMR, 100.6 MHz; δ in ppm | Multiplicity | HMBC | NOESY |
|---|---|---|---|---|---|
| 1A | 5.59 dd (8.64 and 2.5) | 99.6 | CH | C-6 | H-2Aa, H-3Aa, H-5, H-5A, |
| 2Aa | 2.17 (m) | 31.4 | CH$_2$ | C-1A, C-3A, C-4A | H-1A, H-4A, H-2Ae |
| 2Ae | 2.43 (m) | | | | H-1A, H-2Aa, H-3Aa |
| 3Aa | 1.97 (m) | 32.1 | CH$_2$ | C-2A, C-4A | H-1A, H-5A, H-3Ae |
| 3Ae | 2.39 (m) | | | | H-3Aa, H$_3$-6A |
| 4A | 3.69 (m) | 71.3 | CH | C-3A, C-5A, C-6A | H-2Aa, H$_3$-6A |
| 5A | 4.03 dq (8.5 and 6.0) | 77.8 | CH | C-1A, C-3A, C-4A, C-6A | H-1A, H-3Aa, H$_3$-6A |
| 6A | 1.67 d (6.0) | 19.4 | CH$_3$ | C-4A, C-5A | H-4A, H-5A |
| 1C | 5.39 dd (9.6 and 2.0) | 101.7 | CH | C-2 | H-2, H-2Ce, H-3C, H-5C |
| 2Ca | 2.02 ddd (12, 12 and 9.6) | 38.4 | CH$_2$ | C-1C, C-3C, C-4C | H-4C |
| 2Ce | 2.99 ddd (12, 5.0 and 2.0) | | | | H-1C |
| 3C | 4.09 ddd (12, 9.0 and 5.0) | 81.1 | CH | C-1D, C-4C | H-1C, H-1D, H-4C, H-5C, H-2Ce |
| 4C | 3.46 t (9.0) | 76.2 | CH | C-3C, C-5C, C-6C | H-2Ca, H$_3$-6C |
| 5C | 3.67 dq (9.0 and 6.0) | 73.4 | CH | C-1C, C-4C, C-6C | H-1C, H-3C, H$_3$-6C |
| 6C | 1.61 d (6.0) | 19.2 | CH$_3$ | C-4C, C-5C | H-4C, H-5C |
| 1D | 4.85 dd (9.6 and 2.0) | 99.3 | CH | C-3C | H-3C, H-3D, H-2De, H-5D |
| 2Da | 1.93 ddd (12, 12 and 9.6) | 38.6 | CH$_2$ | C-1D, C-3D, C-4D | H-1D |
| 2De | 2.40 ddd (12, 5.0 and 2.0) | | | | |
| 3D | 4.01 ddd (12, 9.0 and 5.0) | 81.0 | CH | C-1E, C-4D | H-1E, H-1D, H-2De, H-5D |
| 4D | 3.46 t (9.0) | 76.0 | CH | C-3D, C-5D | H-2Da, H$_3$-6D |
| 5D | 3.69 dq (9.0 and 6.0) | 73.4 | CH | C-1D, C-4D, C-6D | H-1D, H-3D, H$_3$-6D |
| 6D | 1.55 d (6.0) | 18.8 | CH$_3$ | C-4D, C-5D | H-4D, H-5D |
| 1E | 5.46 dd (9.6 and 2.0) | 98.9 | CH | C-3D | H-5E, H-3D, H-2Ea, H-2Ee |
| 2Ea | 1.85 dd (13.1 and 9.6) | 45.3 | CH$_2$ | C-1E, C-3E, C-4E | H-4E, H-2Ee |
| 2Ee | 2.32 dd (13.1 and 2.0) | | | | H-1E, H-2Ea |
| 3E | — | 71.3 | C | — | — |
| 3E-CH$_3$ | 1.50 (s) | 28.0 | CH$_3$ | C-4E, C-5E, C-3E | H-5E, H$_3$-6E |
| 4E | 3.34 d (9.2) | 77.5 | CH | C-3E-CH$_3$, C-3E, C-5E | H-2aE, H$_3$-3E, H$_3$-6E |
| 5E | 4.28 dq (9.2 and 6.0) | 72.2 | CH | C-3E, C-4E | H$_3$-3E, H$_3$-6E |
| 6E | 1.60 d (6.0) | 19.1 | CH$_3$ | C-1E, C-4E, C-5E | H-1E, H$_3$-6E |

*A = B = C = D = E: sugars

TABLE 12

Antitumor activity assay of derivatives of MTM against tumor cell lines.
Data obtained with MTM are also included as a reference.
The number values refer to GI$_{50}$ (μM), or concentration at which
the compound assayed inhibits 50% of the cell growth compared to non-treated cells.

| | compounds | | | | | | | | | | | |
|---|---|---|---|---|---|---|---|---|---|---|---|---|
| Cell line (cancer type) | MTM | VIII | IX | X | XI | XII | XIII | XVII | XVIII | XIX | XX | XXI |
| MDA-MB-231 (breast) | 0.16 | 0.23 | 1.94 | 0.37 | 0.45 | 1.28 | 1.38 | 3.72 | 0.40 | 0.69 | >10 | 0.47 |
| A549 (lung) | 0.16 | 0.19 | 2.67 | 0.48 | 0.75 | 1.81 | 1.49 | >10 | 0.75 | 0.91 | >10 | 0.44 |
| HT29 (colon) | 0.21 | 0.27 | 3.87 | 0.93 | 0.71 | >10 | 3.19 | >10 | 2.01 | 5.98 | >10 | 0.94 |

VIII = demycarosyl-3D-β-D-digitoxosyl-MTM;

IX = deoliosyl-3C-α-L-digitoxosyl-MTM;

X = deoliosyl-3C-β-D-mycarosyl-MTM;

XI = 3A-deolivosyl-MTM;

XII = demycarosyl-MTM;

XIII = 6-dediolivosyl-6-β-D-amicetosyl-MTM;

XVII = deoliosyl-demycarosyl-3C-β-D-boivinosyl-MTM;

XVIII = 6-dediolivosyl-6-β-D-amicetosyl-deoliosyl-demycarosyl-3C-β-D-boivinosyl-MTM;

XIX = deoliosyl-demycarosyl-3C-β-D-olivosyl-3D-β-D-digitoxosyl-MTM;

XX = 6-dediolivosyl-6-β-D-amicetosyl-deoliosyl-demycarosyl-3C-β-D-olivosyl-3D-β-D-digitoxosyl-MTM;

XXI = 6-dediolivosyl-6-β-D-amicetosyl-deoliosyl-3C-β-D-olivosyl-MTM

The invention claimed is:
1. Compound of formula VIII:

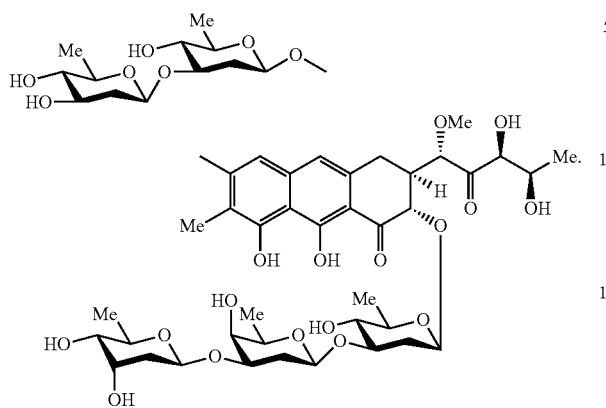

2. A bacterial strain *Streptomyces argillaceus* (pFL942) characterized by having an additional nucleic acid encoding active enzymes for the biosynthesis of sugars which are not present in *Streptomyces argillaceus* wild type.

3. A bacterial strain of claim 2, characterized in that the nucleic acid of *Streptomyces argillaceus* (pFL942) is contained in the plasmid pFL942 and encodes active enzymes for the biosynthesis of L-mycarose and biosynthetic intermediates thereof.

4. A method for obtaining the bacterial strains of claim 2, comprising the introduction of plasmid pFL942 in *Streptomyces argillaceus* which encodes active enzymes for the biosynthesis of sugars which are not present in *Streptomyces argillaceus* wild type.

5. A method for producing a compound of formula VIII comprising:

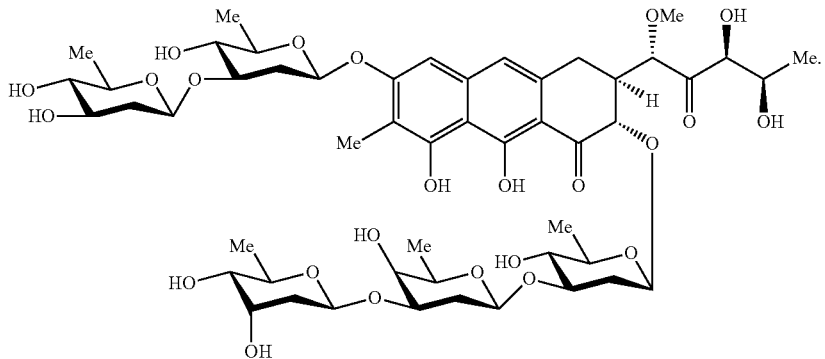

a) culturing a bacterial strain *Streptomyces argillaceus* (pFL942) characterized by having an additional nucleic acid encoding active enzymes for the biosynthesis of sugars which are not present in *Streptomyces argillaceus* wild type in suitable medium; and
b) isolating formula VIII from the culture broth.

6. A pharmaceutical composition comprising an effective amount of the compound of claim 1 or a pharmaceutically acceptable salt thereof together with a pharmaceutically acceptable excipient.

* * * * *

UNITED STATES PATENT AND TRADEMARK OFFICE
CERTIFICATE OF CORRECTION

| | |
|---|---|
| PATENT NO. | : 8,426,169 B2 |
| APPLICATION NO. | : 12/525695 |
| DATED | : April 23, 2013 |
| INVENTOR(S) | : Jürgen Rohr et al. |

Figure 4A:
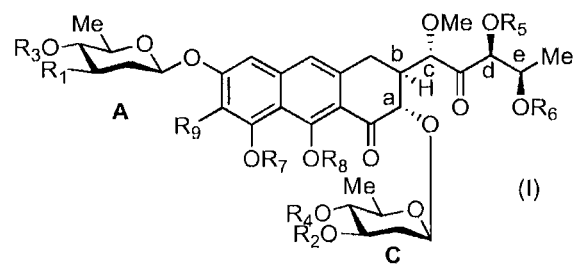
FIG. 4a. Chemical structures of demycarosyl-3D-β-D-digitoxosyl-MTM (formula VIII), deoliosyl-3C-α-L-digitoxosyl-MTM [formula (IX)], deoliosyl-3C-β-D-mycarosyl-MTM [formula (X)], 3A-deolivosyl-MTM [formula (XI)], demycarosyl-MTM [formula (XII)], and 6-dediolivosyl-6-β-D-amicetosyl-MTM [formula (XIII)].
Figure 4A:
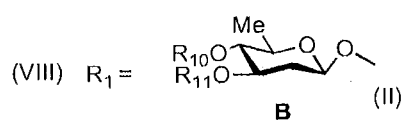
Figure 4A:
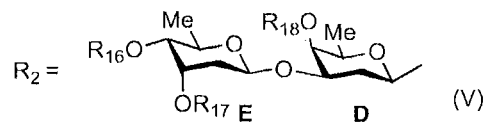
Figure 4A:
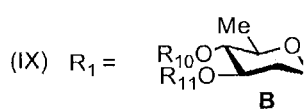
Figure 4A:
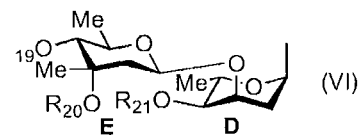
Figure 4A:
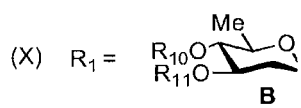
Figure 4A:
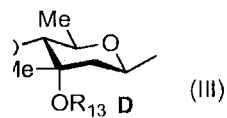
Figure 4A:
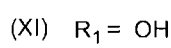
Figure 4A:
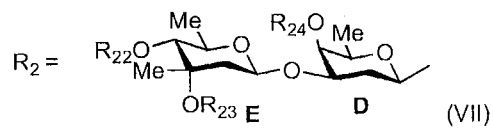
Figure 4A:
Figure 4A:
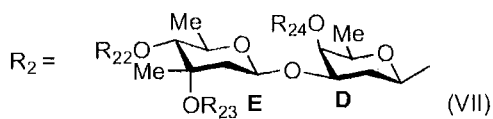
Figure 4A:
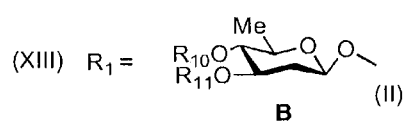
Figure 4A:
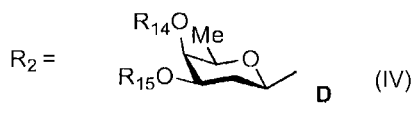
Figure 4B:
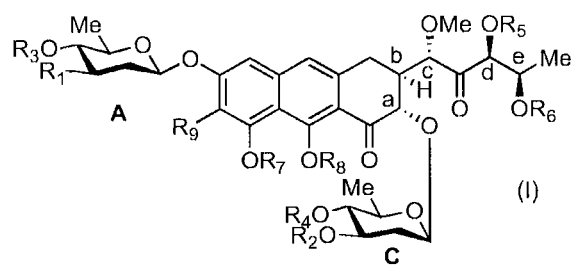
FIG. 4b. Chemical structures of deoliosyl-demycarosyl-3C-β-D-boivinosyl-MTM [formula (XVII)]; 6-dediolivosyl-6-β-D-amicetosyl-deoliosyl-demycarosyl-3C-β-D-boivinosyl-MTM [formula (XVIII)]; deoliosyl-demycarosyl-3C-β-D-olivosyl-3D-β-D-digitoxosyl-MTM [formula (XIX)]; 6-dediolivosyl-6-β-D-amicetosyl-deoliosyl-demycarosyl-3C-β-D-olivosyl-3D-β-D-digitoxosyl-MTM [formula (XX)], and 6-dediolivosyl-6-β-D-amicetosyl-deoliosyl-3C-β-D-olivosyl-MTM [formula (XXI)].
Figure 4B:
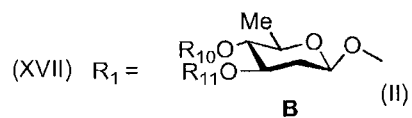
Figure 4B:
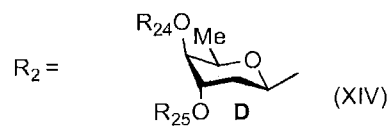
Figure 4B:
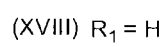
Figure 4B:
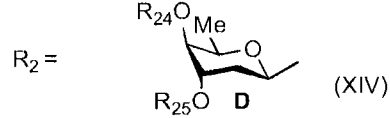
Figure 4B:
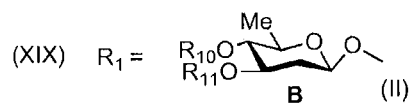
Figure 4B:
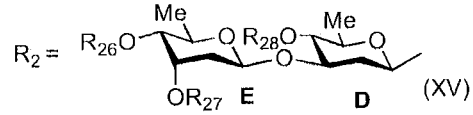
Figure 4B:
Figure 4B:
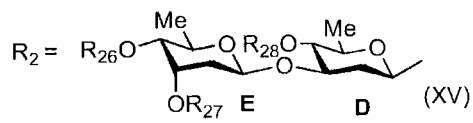
Figure 4B:
Figure 4B:
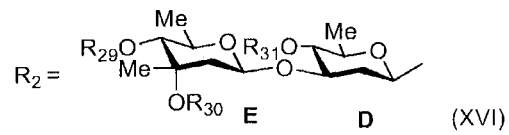
Figure 4A:
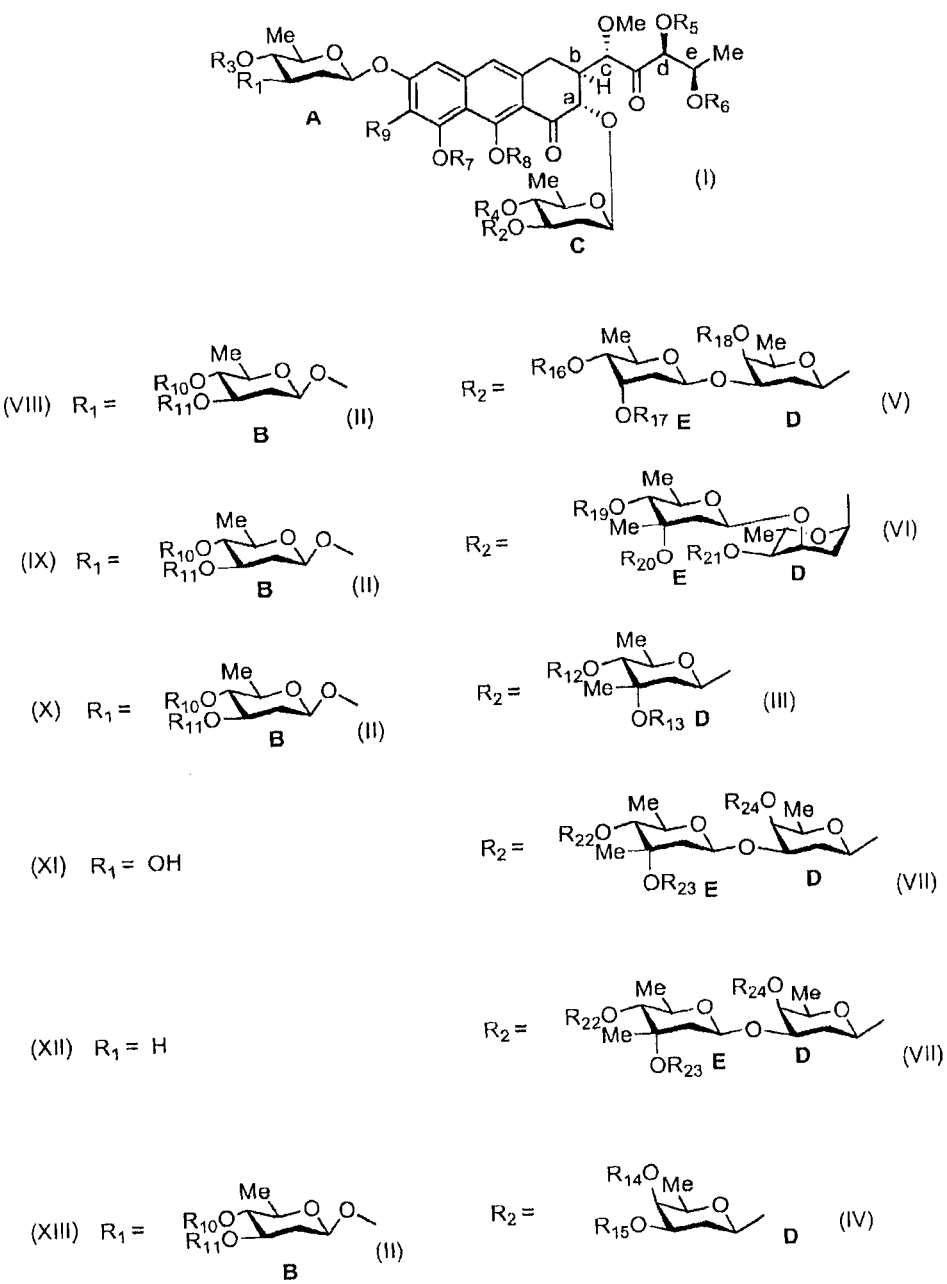

It is certified that error appears in the above-identified patent and that said Letters Patent is hereby corrected as shown below:

In the Drawings:

Drawings Page, Sheet 3 of 4, Page 5, Figure 4a:

Replace with attached drawing.

Signed and Sealed this
Ninth Day of September, 2014

Michelle K. Lee
*Deputy Director of the United States Patent and Trademark Office*